(12) United States Patent
Odagiri

(10) Patent No.: US 11,461,894 B2
(45) Date of Patent: Oct. 4, 2022

(54) INFORMATION PROCESSING APPARATUS, INSPECTION SYSTEM, INFORMATION PROCESSING METHOD, AND STORAGE MEDIUM

(71) Applicant: CANON KABUSHIKI KAISHA, Tokyo (JP)

(72) Inventor: Jun Odagiri, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 164 days.

(21) Appl. No.: 16/996,597

(22) Filed: Aug. 18, 2020

(65) Prior Publication Data
US 2021/0065365 A1    Mar. 4, 2021

(30) Foreign Application Priority Data
Aug. 26, 2019 (JP) .............................. JP2019-154070

(51) Int. Cl.
*G06T 7/00* (2017.01)
(52) U.S. Cl.
CPC .. *G06T 7/0012* (2013.01); *G06T 2207/10132* (2013.01)
(58) Field of Classification Search
CPC ......... G06T 7/0012; G06T 2207/10132; G06T 7/0014; G06T 7/00; G06T 7/0002
See application file for complete search history.

(56) References Cited

U.S. PATENT DOCUMENTS

| 6,463,552 B1* | 10/2002 | Jibbe ................... G06F 9/45512 |
| | | 714/33 |
| 2015/0051489 A1* | 2/2015 | Caluser .................. A61B 8/466 |
| | | 600/440 |
| 2017/0360403 A1* | 12/2017 | Rothberg ................. A61B 8/06 |
| 2018/0228460 A1 | 8/2018 | Singh |
| 2021/0065370 A1* | 3/2021 | Kotoku ..................... G06T 7/74 |

FOREIGN PATENT DOCUMENTS

JP          2018-175007 A        11/2018

* cited by examiner

*Primary Examiner* — John J Lee
(74) *Attorney, Agent, or Firm* — Canon U.S.A., Inc., IP Division

(57) ABSTRACT

An information processing apparatus comprises: acquiring a first image including at least a part of an inspection device and a second image including at least a part of a subject; estimating a position of the inspection device based on the first image; estimating position and orientation information for the subject based on the second image; identifying an inspection region of the subject from results of estimating; and receiving a finalization instruction to finalize an inspection result to be recorded or output to an external apparatus based on sequentially acquired inspection results of the subject, and a finalization instruction to finalize inspection region information to be recorded or output to the external apparatus in association with the inspection result, wherein the finalization instruction for the inspection region information is received before the finalization instruction for the inspection result.

16 Claims, 21 Drawing Sheets

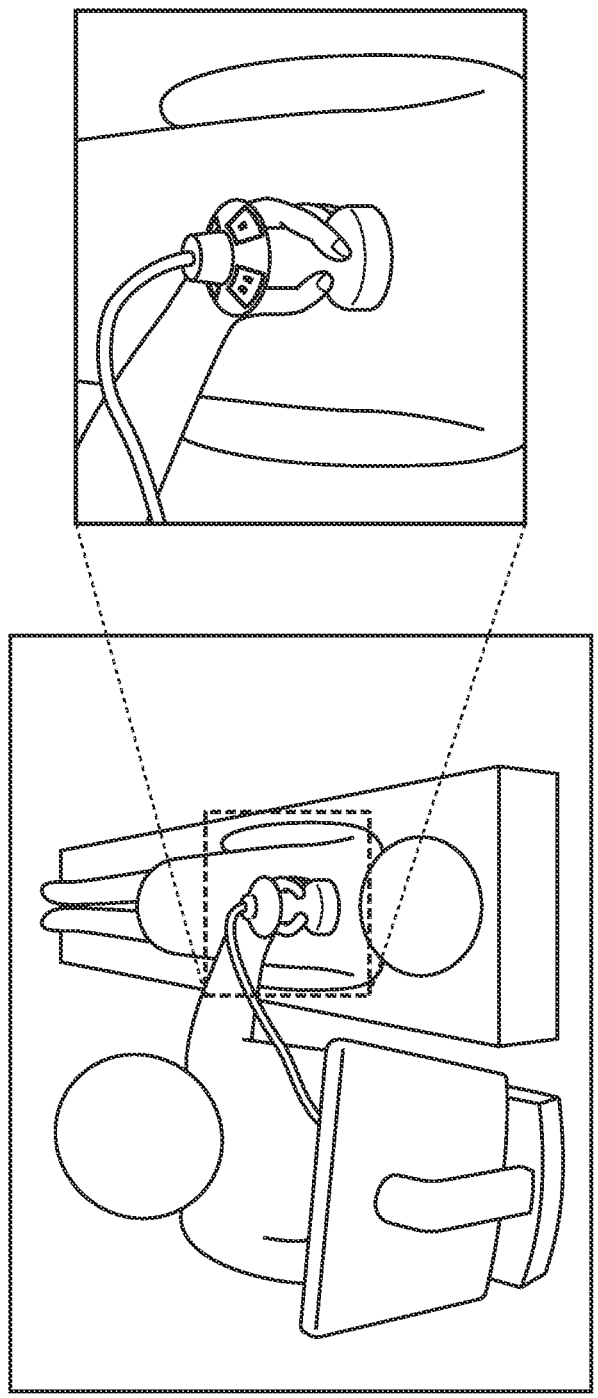

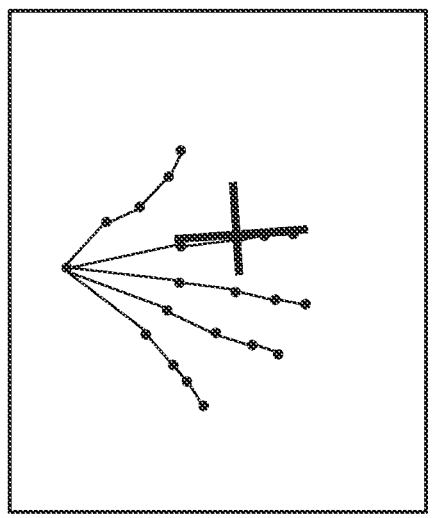
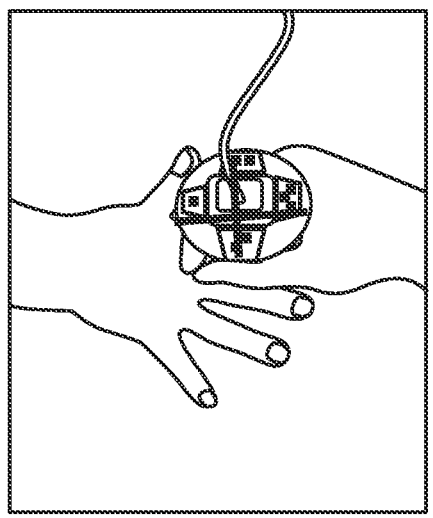
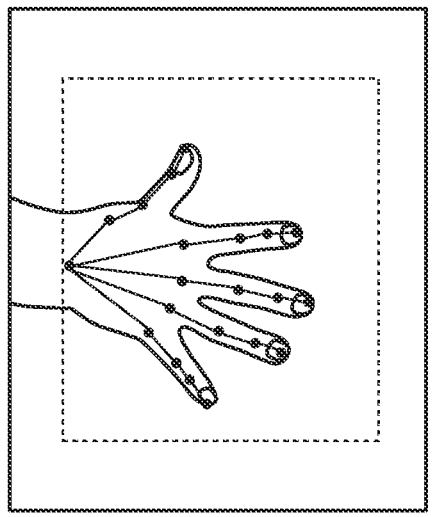

INFORMATION PROCESSING APPARATUS, INSPECTION SYSTEM, INFORMATION PROCESSING METHOD, AND STORAGE MEDIUM

BACKGROUND

Field

The present disclosure relates to an information processing apparatus used for diagnoses based on medical images in the medical field, an inspection system, an information processing method, and a storage medium.

Description of the Related Art

In the medical field, doctors make diagnoses by using medical images captured by various modalities (inspection systems). Modalities include ultrasonic diagnostic apparatuses, photoacoustic imaging apparatuses (hereinafter referred to as photoacoustic tomography (PAT) apparatuses), magnetic resonance imaging (MRI) apparatuses, and computer tomography apparatuses (hereinafter referred to as X-ray computed tomography (CT) apparatuses). Japanese Patent Laid-Open No. 2018-175007 discusses a system for determining (identifying) which portion of a subject is image-captured for medical images to be used for diagnoses on these apparatuses, based on the positional relation between an inspection system and the subject.

More specifically, the system captures inspection images and then acquires an outer appearance image in which the subject under inspection and a probe are captured. The system then identifies the positions of the subject and the probe based on the acquired outer appearance image and then automatically calculates an inspection region based on the relation between the two positions.

However, according to the procedures discussed in Japanese Patent Laid-Open No. 2018-175007, the identification of a region calculated from a camera image captured at the same time may fail, or incorrect estimation may occur despite a suitable ultrasonic image having been acquired. In such a case, the inspector needs to attempt to re-acquire an ultrasonic image and a camera image while suitably bringing the ultrasonic probe into contact with the subject again. This results in a burden on both the inspector and the subject and this is an issue. Moreover, there is another issue associated with giving up automatic data entry using a camera that results in the inspector needing to manually operate a control panel to enter region information. This is a burden on both the inspector and the subject.

SUMMARY

The present disclosure in its first aspect provides an information processing apparatus comprising: at least one processor; and a memory storing instructions that, when executed by the at least one processor, cause the at least one processor to: acquire a first image including at least a part of an inspection device and a second image including at least a part of a subject, the first and the second images being captured by an imaging apparatus; estimate, as a first estimation, a position of the inspection device based on the first image; estimate, as a second estimation, position and orientation information for the subject based on the second image; identify an inspection region of the subject from a result of the first estimation and a result of the second estimation; and receive a finalization instruction to finalize an inspection result to be recorded or output to an external apparatus based on sequentially acquired inspection results of the subject, and a finalization instruction to finalize inspection region information to be recorded or output to the external apparatus in association with the inspection result, wherein the finalization instruction for the inspection region information is received before the finalization instruction for the inspection result.

The present disclosure in its second aspect provides an inspection system comprising: an imaging apparatus configured to capture a first image including at least a part of an inspection device and a second image including at least a part of a subject; at least one processor; and a memory storing instructions that, when executed by the at least one processor, cause the at least one processor to: inspect a subject; estimate, as a first estimation, a position of the inspection device based on the first image; estimate, as a second estimation, position and orientation information for the subject based on the second image; identify an inspection region of the subject from a result of the first estimation and a result of the second estimation; and receive a finalization instruction to finalize an inspection result to be recorded or output to an external apparatus based on sequentially acquired inspection results, and a finalization instruction to finalize inspection region information to be recorded or output to the external apparatus in association with the inspection result, wherein the finalization instruction for the inspection region information is received before the finalization instruction for the inspection result.

The present disclosure in its third aspect provides an information processing method comprising: acquiring a first image including at least a part of an inspection device and a second image including at least a part of a subject, the first and the second images being captured by an imaging unit; estimating, as first estimating, a position of the inspection device based on the first image; estimating, as second estimating, position and orientation information for the subject based on the second image; identifying an inspection region of the subject from a result of the first estimating and a result of the second estimating; and receiving a finalization instruction to finalize an inspection result to be recorded or output to an external apparatus based on sequentially acquired inspection results of the subject, and a finalization instruction to finalize inspection region information to be recorded or output to the external apparatus in association with the inspection result, wherein the finalization instruction for the inspection region information is received before the finalization instruction for the inspection result.

The present disclosure in its fourth aspect provides a non-transitory computer-readable storage medium storing instructions that, when executed by at least one processor of an information processing apparatus, configure the at least one processor of the information processing apparatus to perform operations comprising: acquire a first image including at least a part of an inspection device and a second image including at least a part of a subject, the first and the second images being captured by an imaging apparatus; estimate, as a first estimation, a position of the inspection device based on the first image; estimate, as a second estimation, position and orientation information for the subject based on the second image; identify an inspection region of the subject from a result of the first estimation and a result of the second estimation; and receive a finalization instruction to finalize an inspection result to be recorded or output to an external apparatus based on sequentially acquired inspection results of the subject, and a finalization instruction to finalize inspection region information to be recorded or output to the external apparatus in association with the inspection result, wherein the finalization instruction for the inspection region information is received before the finalization instruction for the inspection result.

Further features of the present disclosure will become apparent from the following description of exemplary embodiments with reference to the attached drawings.

BRIEF DESCRIPTION OF THE DRAWINGS

FIG. 16 illustrates images of an outer appearance image and markers supplied to the probe captured in the outer appearance image according to the first exemplary embodiment.

FIGS. 19A, 19B, and 19C illustrate images of screens displayed on the display in identifying an inspection region after ultrasonic image determination according to the first exemplary embodiment.

DESCRIPTION OF THE EMBODIMENTS

[First Exemplary Embodiment]

A first exemplary embodiment will be described below with reference to the accompanying drawings.

Figure 1:
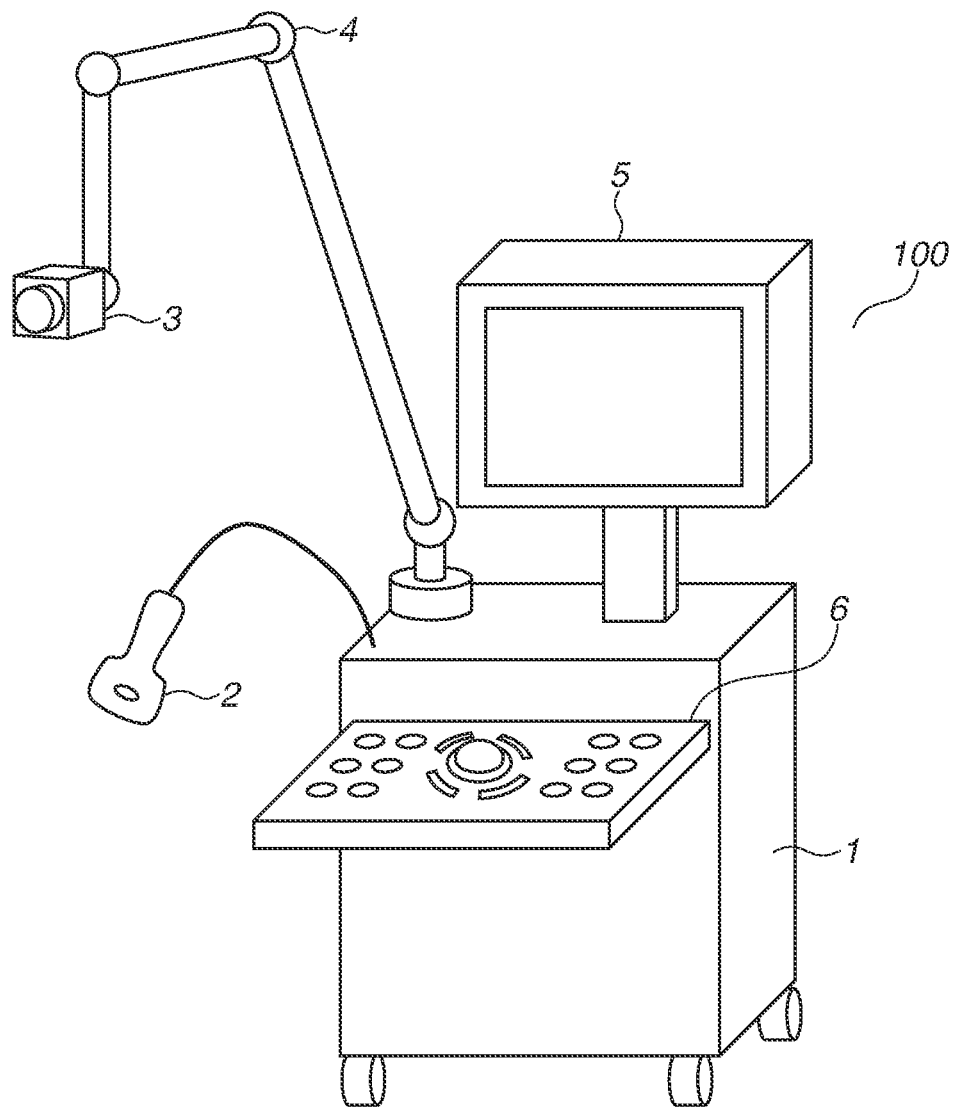
FIG. 1 illustrates an example of a configuration of an inspection system according to a first exemplary embodiment.

FIG. 1 is an overall view illustrating an ultrasonic diagnostic apparatus 100 as an example of an inspection system according to the first exemplary embodiment. An information processing apparatus according to the present disclosure is also applicable to an optional electronic apparatus capable of processing a captured image. These electronic apparatuses may include portable phones, tablet terminals, personal computers, and information terminals of clock type or eyeglass type.

The ultrasonic diagnostic apparatus 100 includes an ultrasonic diagnostic apparatus body 1, an ultrasonic probe 2, a camera 3, an arm 4, a display 5, and a control panel 6. The housing of the ultrasonic diagnostic apparatus body 1 includes therein a computer including various control units, a power source, and a communication interface (I/F), as an information processing apparatus.

The ultrasonic probe 2 transmits and receives ultrasonic waves in a state where an end surface thereof is in contact with the surface of a subject. The ultrasonic probe 2 includes a plurality of piezoelectric vibrators that are one-dimensionally arranged (arranged in single row) at the end surface. The ultrasonic probe 2 scans a scan area while transmitting ultrasonic waves into the subject body by using each piezoelectric vibrator, and receives reflected waves from the subject as echo signals. Usable scanning methods include B-mode scan, Doppler mode scan, and any other scanning methods.

Figure 2:
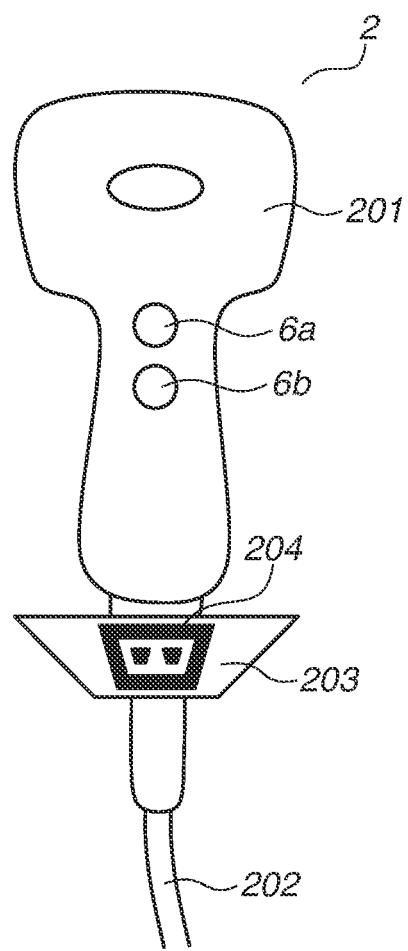
FIG. 2 illustrates an example of a configuration of a probe according to the first exemplary embodiment.

FIG. 2 illustrates an outer appearance of the ultrasonic probe 2. The ultrasonic probe 2 includes an ultrasonic probe body 201, a connector 202, a marker attachment 203, a marker 204, a freeze button 6a, and a finalization button 6b.

A camera 3 installed at an end of the arm 4 disposed on the ultrasonic diagnostic apparatus body 1 can be used to capture the state around the ultrasonic diagnostic apparatus 100. According to the present exemplary embodiment, the camera 3 is mainly used to capture an outer appearance image for identifying an inspection region at the time of inspection on the subject using the ultrasonic probe 2. More specifically, at the time of inspection on the subject using the ultrasonic probe 2, the camera 3 captures an outer appearance image including the subject's inspection region and the ultrasonic probe 2.

The camera 3 includes an imaging optical system, an image sensor, a central processing unit (CPU), an image processing circuit, a read only memory (ROM), a random access memory (RAM), and at least one communication I/F as a configuration of an ordinary camera. An image is captured when a light flux from the subject is formed on the image sensor including a charge coupled device (CCD) sensor and a complementary metal oxide (CMO) step S sensor through the imaging optical system including lenses and other optical elements. The imaging optical system includes a lens group. The camera 3 includes a lens drive control unit for controlling zoom and focus by driving the lens group along the optical axis. An electrical signal output from the image sensor is converted into digital image data by an analog-to-digital (A/D) converter. The digital image data is subjected to various image processing by an image processing circuit, and the resultant is output to an external apparatus. Instead of being subjected to the image processing by the image processing circuit, the digital image data may be output to the external apparatus via the communication I/F and then processed by the processing unit of the external apparatus.

According to the present exemplary embodiment, the camera 3 uses an image sensor that mainly receives light of the visible light region to capture an image. However, an example of the camera 3 is not limited thereto but may be a camera that receives light of the infrared light region to capture an image, or a camera that receives light of a plurality of wavelength regions, such as visible light and infrared light, to capture an image. In addition, the camera 3 may be a stereo camera capable of not only outer appearance image capturing but also distance measurement, or a camera having a Time-of-Flight (ToF) sensor for distance measurement. Hereinafter, an image captured by the camera 3 is referred to as a camera image.

The arm 4 is installed in the ultrasonic diagnostic apparatus body 1, and is used to dispose the camera 3 at a position and orientation at and in which an outer appearance image including the subject's inspection region and the ultrasonic probe 2 are enabled to be captured. According to the present exemplary embodiment, the arm 4 is a serial link mechanism arm having five joints. The joint at the end of the arm 4 that is connected to the camera 3 is a ball joint that enables easily setting the orientation of the camera 3.

The display 5 including a display device, such as a liquid crystal display (LCD), displays images input from the ultrasonic diagnostic apparatus body 1, menu screens, and graphical user interfaces (GUIs). The display 5 displays an image stored in a memory 8 and an image recorded in a nonvolatile memory on the display device. The display 5 is an apparatus for displaying ultrasonic images, camera images, body mark images, probe mark images, and region identification results under the control of the CPU 7. A body mark image is an image simply expressing the body shape and is generally used for ultrasonic diagnostic apparatuses. A probe mark is displayed while being superimposed on a body mark image, and is applied for the purpose of identifying the angle at which the ultrasonic probe 2 contacts the contact surface on the subject body.

The control panel 6 includes a keyboard, a track ball, switches, dials, and a touch panel. The control panel 6 receives various input operations performed by an inspector by using these operating members. Various input operations include an imaging instruction to perform image capturing using the ultrasonic probe 2 and image capturing using the camera 3, an instruction to display various images, and an instruction to perform image switching, mode selection, and various settings. A received input operation signal is input to the ultrasonic diagnostic apparatus body 1 and then reflected to the control performed on each unit by the CPU 7. If a touch panel is employed, the touch panel may be integrated with the display 5. The inspector can make various settings and perform operations on the ultrasonic diagnostic apparatus body 1 by performing touch and drag operations on the buttons displayed on the display 5.

When the inspector operates the freeze button 6a in a state where signals are being sequentially acquired from the ultrasonic probe 2 and the ultrasonic image in the memory 8 is being updated, signals from the ultrasonic probe 2 stop, and the update of the ultrasonic image in the memory 8 is suspended. At the same time, signals from the camera 3 also stop, and the update of the camera image in the memory 8 is suspended. In a case where the inspector operates the freeze button 6a in a state where the update is stopped, signals are received from the ultrasonic probe 2 again, the update of the ultrasonic image in the memory 8 is started, and the update of the camera image is also started in a similar manner. When the inspector operates the finalization button 6b in a state where one ultrasonic image is fixed by the depression of the freeze button 6a, the CPU 7 stores the ultrasonic image in the nonvolatile memory 9. The freeze button 6a and the finalization button 6b may be provided not on the control panel 6 but on the ultrasonic probe 2.

Figure 3:
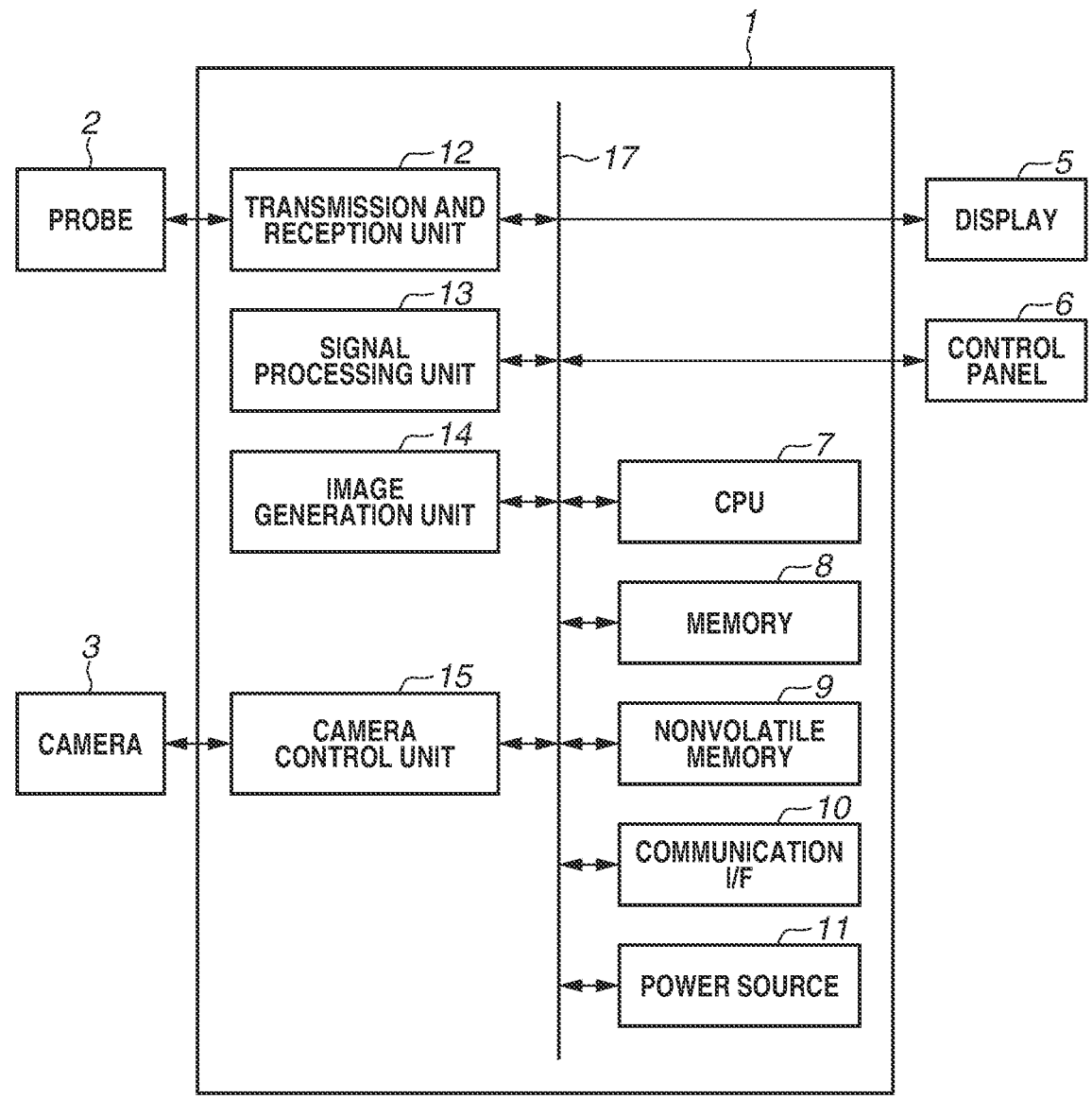
FIG. 3 is a block diagram illustrating an example of the configuration of the inspection system according to the first exemplary embodiment.

FIG. 3 is a block diagram illustrating a configuration of the ultrasonic diagnostic apparatus body 1. The ultrasonic diagnostic apparatus body 1 includes a transmission and reception unit 12, a signal processing unit 13, an image generation unit 14, a camera control unit 15, the CPU 7, the memory 8, the nonvolatile memory 9, and a communication I/F 10 which are all connected to an internal bus 17. These units connected to the internal bus 17 are configured to exchange data with each other via the internal bus 17.

The memory 8 includes a RAM (such as a volatile memory using semiconductor elements). The CPU 7 controls each unit of the ultrasonic diagnostic apparatus body 1 by using the memory 8 as a work memory in accordance with a program stored, for example, in the nonvolatile memory 9. The nonvolatile memory 9 stores image data, subject data, and various programs for operating the CPU 7. The nonvolatile memory 9 includes a hard disk (HD) and a ROM.

The transmission and reception unit 12 includes at least one communication I/F for supplying power to the ultrasonic probe 2, transmitting control signals to the ultrasonic probe 2, and receiving an echo signal from the ultrasonic probe 2. The transmission and reception unit 12 supplies to the ultrasonic probe 2 a signal for instructing the ultrasonic probe 2 to emit an ultrasonic beam based on, for example, a control signal from the CPU 7. The transmission and reception unit 12 further receives a reflection signal, i.e., an echo signal, from the ultrasonic probe 2, subjects the received signal to phasing addition, and outputs the signal acquired through the phasing addition to the signal processing unit 13.

The signal processing unit 13 includes a B-mode processing unit (or Bc-mode processing unit), a Doppler mode processing unit, and a color Doppler mode processing unit. The B-mode processing unit performs imaging on amplitude information of the receive signal supplied from the transmission and reception unit 12 through known processing to generate B-mode signal data. The Doppler mode processing unit extracts Doppler deviation frequency components from the receive signal supplied from the transmission and reception unit 12 through known processing. Then, the Doppler mode processing unit subjects the receive signal to Fast Fourier Transform (FFT) processing to generate Doppler signal data as blood flow information. The color Doppler mode processing unit performs imaging on the blood flow information based on the receive signal supplied from the transmission and reception unit 12 through known processing to generate color Doppler mode signal data. The signal processing unit 13 outputs the generated various data to the image generation unit 14.

The image generation unit 14 generates two- and/or three-dimensional ultrasonic images regarding the scan area through known processing, based on the data supplied from the signal processing unit 13. For example, the image generation unit 14 generates volume data regarding the scan area based on the supplied data. On the basis of the generated volume data, the image generation unit 14 generates two-dimensional ultrasonic image data through the Multi-Planar Reconstruction (MPR) processing, and/or three-dimensional ultrasonic image data through the volume rendering processing. The image generation unit 14 outputs the generated two- and three-dimensional ultrasonic images to the display 5. Examples of ultrasonic images include a B-mode image, a Doppler mode image, a color Doppler mode image, and an M-mode image.

Each of the transmission and reception unit 12, the signal processing unit 13, the image generation unit 14, and the camera control unit 15 may be implemented by hardware such as an Application Specific Integrated Circuit (ASIC) and a Programmable Logic Array (PLA). In addition, these units may be implemented by a programmable processor, such as a CPU and a Microprocessor Unit (MPU) executing software, or implemented by a combination of software and hardware.

The camera control unit 15 includes at least one communication I/F for supplying power to the camera 3 and transmitting and receiving control signals and image signals to/from the camera 3. The camera 3 may be provided with a power source for single unit operation without being supplied with power from the ultrasonic diagnostic apparatus body 1. The camera control unit 15 can control various imaging parameters of the camera 3, for example, zoom, focus, and diaphragm values, by transmitting control signals to the camera 3 via the communication I/F. The camera 3 may be provided with a tripod head that can be automatically panned and tilted, and configured to receive a pan tilt control signal and perform position and orientation control through pan tilt drive. In addition, a drive unit and a drive control unit for electrically controlling the position and orientation of the camera 3 may be disposed at the end of the arm 4. In such a case, the position and orientation of the camera 3 may be controlled based on control signals from the camera control unit 15 or the CPU 7.

<Processing Flow>

Figure 4:
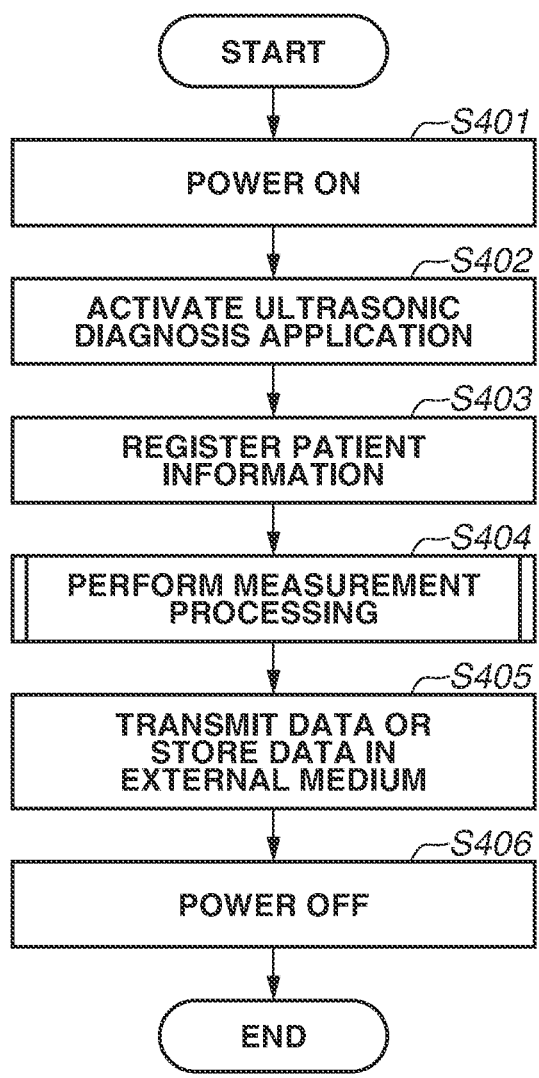
FIG. 4 is a flowchart illustrating overall processing of the inspection system according to the first exemplary embodiment.

FIG. 4 is a flowchart illustrating a processing flow performed by the CPU 7 to implement overall operations of inspection processing which is performed by the ultrasonic diagnostic apparatus 100. More specifically, the operations in the following steps are executed by the CPU 7 or each unit under the instruction of the CPU 7.

In step S401, the CPU 7 turns power ON in response to an inspector's operation, and loads an operating system (OS) stored in the nonvolatile memory 9. In step S402, the CPU 7 automatically activates an ultrasonic diagnostic application. At this timing, the CPU 7 transmits an image signal of the activation screen to the display 5 to display the activation screen.

After the ultrasonic diagnostic application is activated and then the initialization processing is completed, the CPU 7 changes the display screen on the display 5 to a subject information registration screen. In step S403, the CPU 7 receives an instruction to register the subject information based on an inspector's operation on the control panel 6. The subject information includes inspection region information in relation to the condition of the subject (mammary gland, heart, artery, abdomen, carotid, thyroid gland, vein, etc.), subject identifier (ID), name, gender, date of birth, age, height, weight, and hospitalization or outpatient. After input of the subject information, when the inspector presses the start button of the control panel 6 (on the display or operation panel), the CPU 7 stores the subject information in the memory 8 or the nonvolatile memory 9. Then, the CPU 7 changes the display screen on the display 5 to the measurement screen of the ultrasonic diagnostic application.

In step S403, the CPU 7 also receives the setting about whether to manually or automatically set the inspection region. The flowchart in a case where the setting for manually setting the inspection region is made will be described below with reference to FIG. 5. The flowchart in a case where the setting for automatically setting the inspection region is made (first and second modifications) will be described below with reference to FIGS. 7 and 11.

After the measurement screen of the ultrasonic diagnostic application is displayed, then in step S404, the CPU 7 performs measurement processing for ultrasonic diagnosis in accordance with an inspector's operation. The measurement processing will be described in detail below.

Upon completion of inspection of all regions, then in step S405, the CPU 7 stores inspection data obtained in the inspection in the nonvolatile memory 9 or an external medium (not illustrated) or transfers the inspection data to an external apparatus (external server) via the communication I/F 10.

When the entire processing is completed and the inspector turns power OFF, then in step S406, the CPU 7 performs processing of ending the ultrasonic diagnostic application and the OS to complete the series of processing.

Figure 5:
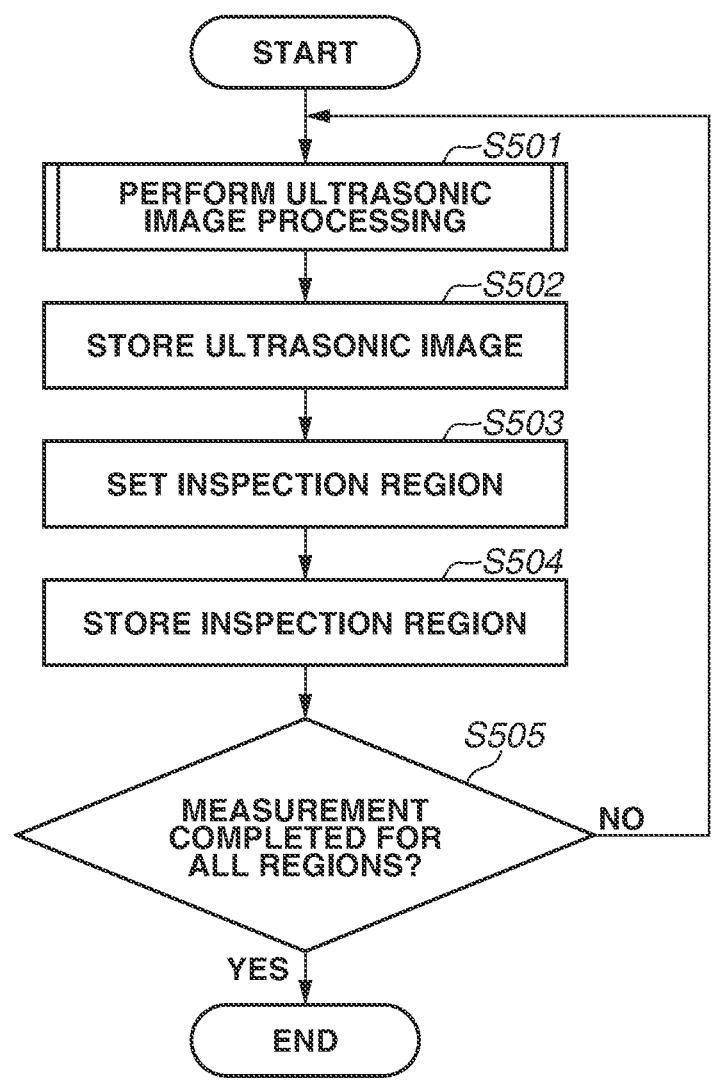
FIG. 5 is a flowchart illustrating measurement processing according to the first exemplary embodiment.

FIG. 5 is a flowchart illustrating a processing flow of the measurement processing in step S404 illustrated in FIG. 4 in a case where the inspector makes the setting for manually setting the inspection region. Each of the following steps is executed by the CPU 7 or each unit under the instruction of the CPU 7.

In step S501, the CPU 7 subjects the echo signal received from the ultrasonic probe 2 to signal processing and image processing to generate an ultrasonic image, and displays the ultrasonic image on the display 5. The ultrasonic image processing in step S501 will be described in detail below.

When the inspector checks the ultrasonic image displayed on the display 5, and if a desired ultrasonic image becomes obtainable, the CPU 7 finalizes the ultrasonic image based on an inspector's operation. In step S502, the CPU 7 stores the ultrasonic image in the memory 8.

In step S503, to record information about where the inspection region is, inspection regions such as body marks and probe marks are set in accordance with an inspector's operation. Annotations, such as comments and arrows, may be input to the display 5 in accordance with an inspector's operation.

When the inspector presses the finalization button 6b, then in step S504, the CPU stores the information about the inspection region in the memory 8.

Upon completion of the measurement processing for a certain inspection region, then in step S505, the CPU 7 determines whether the measurement is completed for all the inspection regions predetermined based on inspection items. If the inspection is not completed for any inspection region (NO in step S505), the processing returns to step S501. Then, the CPU 7 performs the measurement processing again. The information about inspection items is classified and recorded in the nonvolatile memory 9 based on the inspection region and symptom in advance. Then, the information is selected from classified and recorded information and set based on an inspector's operation. If the measurement processing is completed for all the inspection regions (YES in step S505), the CPU 7 ends the processing in step S404.

Figure 6:
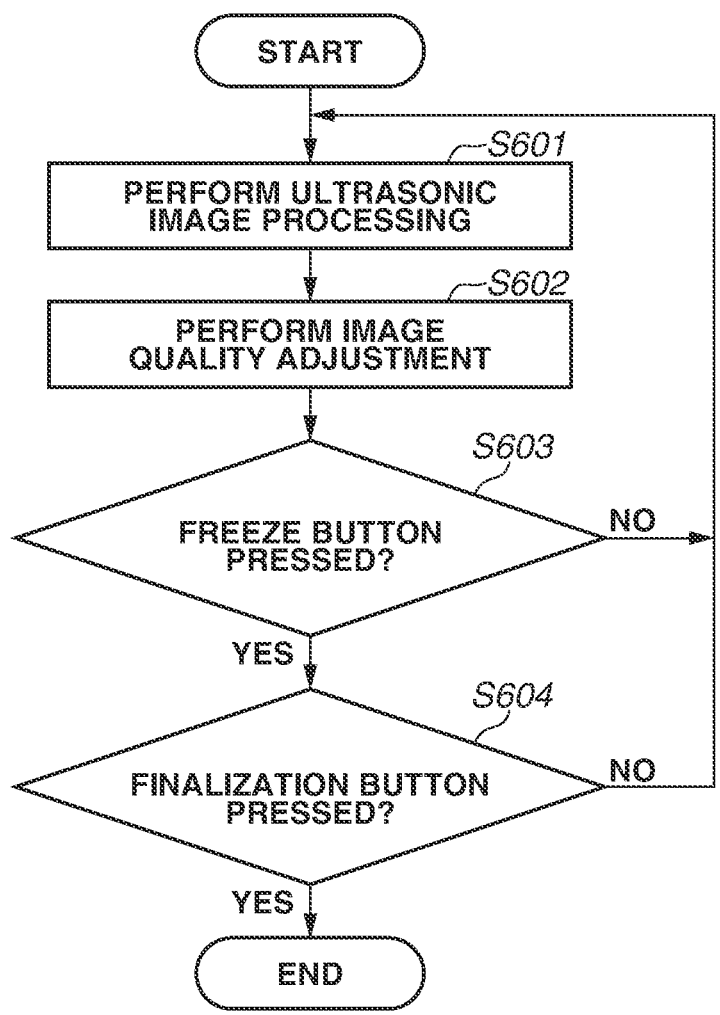
FIG. 6 is a flowchart illustrating ultrasonic image processing according to the first exemplary embodiment.

FIG. 6 is a flowchart illustrating a detailed flow of the ultrasonic image processing in step S501. Each of the following steps is executed by the CPU 7, or the signal processing unit 13 and the image generation unit 14 under the instruction of the CPU 7.

As described above, the ultrasonic probe 2, which is an example of an inspection device, scans the scan area while transmitting ultrasonic waves into the subject body by using each piezoelectric vibrator, and receives the reflected wave from the subject as an echo signal (ultrasonic signal). According to the present exemplary embodiment, the ultrasonic probe 2 is configured to be operable by the inspector with the ultrasonic probe 2 in their hand. In step S601, the signal processing unit 13 and the image generation unit 14 subject the ultrasonic signals transmitted from the ultrasonic probe 2, to signal processing and image processing, respectively, to generate an ultrasonic image. The CPU 7 then displays the ultrasonic image on the display 5. To obtain the desired image, the inspector can further adjust and correct various processing parameters by using the control panel 6 while monitoring the ultrasonic image displayed on the display 5. More specifically, in step S602, various parameters (mode, gain, focus, echo level, etc.) are changed based on operation signals accepted by the control panel 6, and the ultrasonic image after the change is regenerated and displayed on the display 5.

In step S603, the CPU 7 determines whether the freeze button 6a provided on the ultrasonic probe 2 is pressed. If the freeze button 6a is not pressed (NO in step S603), the CPU 7 repeats steps S601 and S602. If the freeze button 6a is pressed (YES in step S603), the CPU 7 determines that the desired ultrasonic image has been acquired, displays the ultrasonic image captured and generated at this timing on the display 5. The CPU 7 then ends the ultrasonic image processing.

Figure 7:
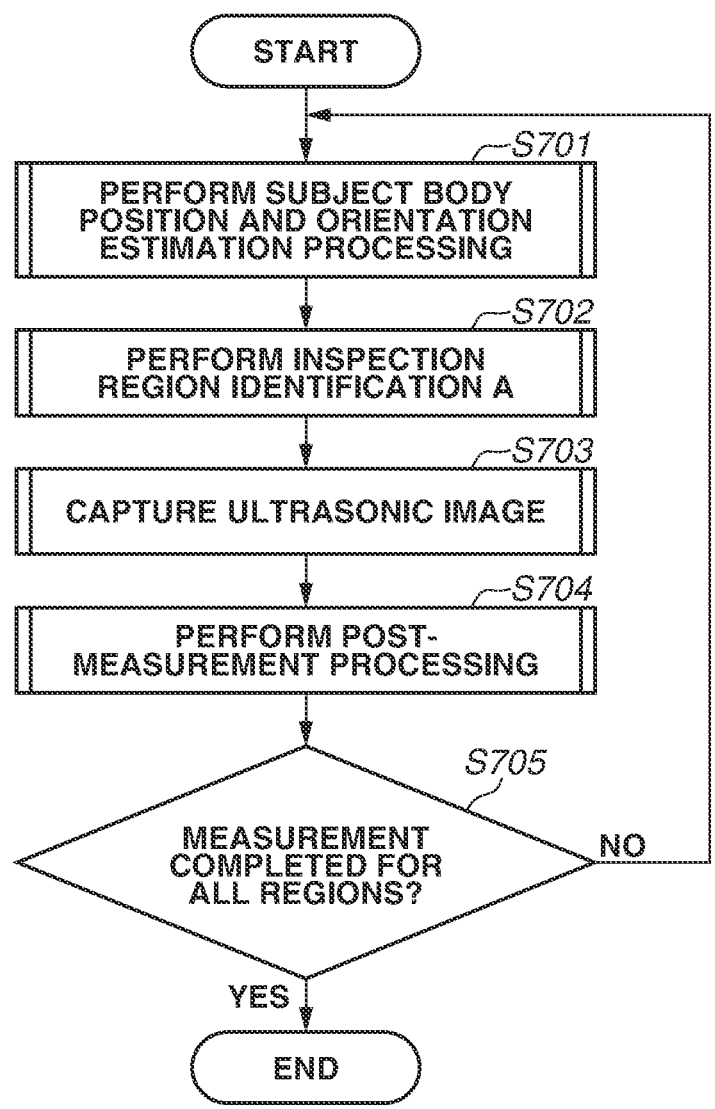
FIG. 7 is a flowchart illustrating the measurement processing according to a first modification of the first exemplary embodiment.

FIG. 7 is a flowchart illustrating another form of the detailed flow of the measurement processing in step S404 illustrated in FIG. 4 in a case where the inspector makes the setting for automatically setting the inspection region. Each of the following steps is executed by the CPU 7 or each unit under the instruction of the CPU 7.

According to a first modification, in step S503 illustrated in FIG. 5, the CPU 7 automatically sets the inspection region performed based on an inspector's operation.

In step S701, the CPU 7 estimates the position and orientation of the subject lying on a bed based on the image acquired by the camera 3. When a result of estimating the position and orientation of the subject is finalized based on an inspector's operation, the CPU 7 stores the position and orientation of the subject in the memory 8. This processing will be described in detail below. In step S702, the CPU 7 estimates the position and orientation of the probe 2 by using the image acquired by the camera 3, automatically identifies the subject's inspection region based on the estimation result for the subject in step S701, and displays the inspection region on the display 5. This processing will be described in detail below.

In step 703, when the freeze button 6a on the control panel 6 or the ultrasonic probe 2 is pressed by the inspector, the update of the ultrasonic image on the display 5 is stopped. If the ultrasonic image is the desired one, the processing proceeds to step S704 based on the depression of the finalization button 6b by the inspector. In step S704, the CPU 7 performs post-measurement processing. Upon completion of the measurement processing for a certain inspection region, then in step S705, the CPU 7 determines whether the measurement is completed for all the inspection regions predetermined based on the inspection items. If the inspection is not completed for any inspection region (NO in step S705), the processing returns to step S701.

According to the present exemplary embodiment as described above, if an inspection region is identified in step S702 before an ultrasonic image in step S1002 is captured, the inspector can concentrate on the determination of the ultrasonic image when capturing an ultrasonic image in step S1002. Although the CPU 7 acquires a camera image in step S703, this camera image is used only for the estimation of the position and orientation of the probe 2 and the screen display but not used for the inspection region identification. The processing in step S703 will be described in detail below with reference to FIG. 10.

Figure 8:
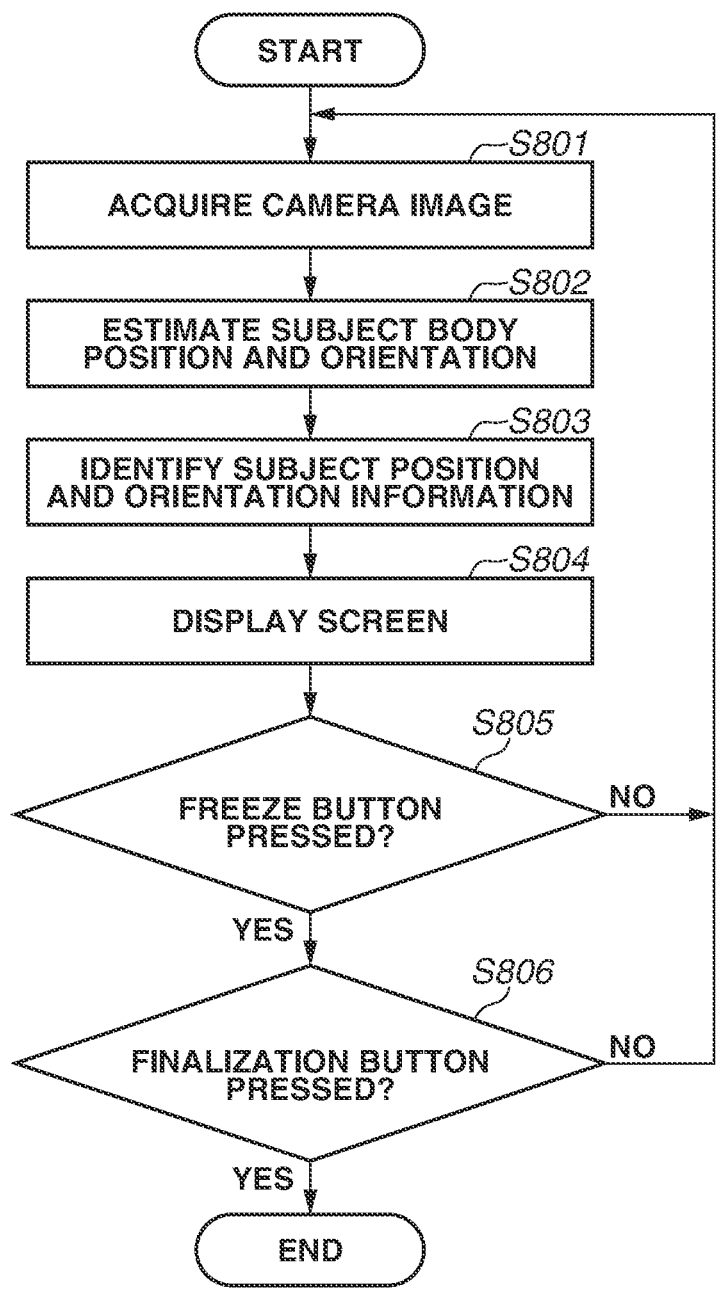
FIG. 8 is a flowchart illustrating processing of estimating the position and orientation of a human body according to the first exemplary embodiment.

FIG. 8 is a flowchart illustrating a detailed flow of processing of estimating the position and orientation of the subject body in step S701 illustrated in FIG. 7. Each operation in the following steps is executed by the CPU 7 or each unit under the instruction of the CPU 7.

Figure 15A:
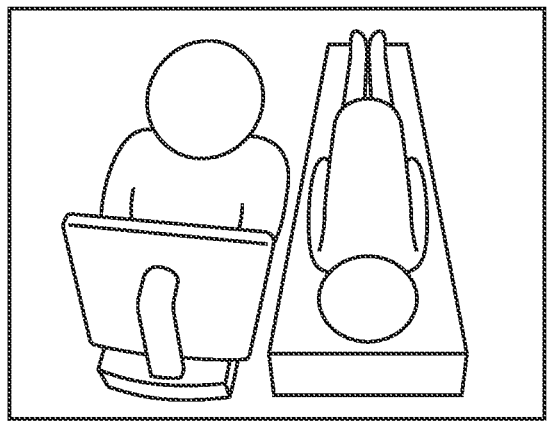
FIGS. 15A, 15B, 15C, and 15D illustrate images of output results obtained in measurement using the inspection system according to the first exemplary embodiment.

In step S801, the CPU 7 instructs the camera control unit 15 to capture the subject lying on the bed by using the camera 3, as illustrated in FIG. 15A. The camera 3 sequentially performs imaging at a predetermined frame rate, and the CPU 7 receives outer appearance images via the communication I/F of the camera control unit 15, and sequentially displays the images on the display 5.

The inspector adjusts the position of the arm 4 so that at least an inspection region of interest, which is a part of the subject, fits into the angle of field of the camera 3, while checking the outer appearance image displayed on the display 5. The display 5 may display a line for guiding the inspector where to bring the position of the subject's inspection region in the displayed outer appearance image by adjusting the position of the camera 3. In such a case, the line for guidance (i.e., GUI data to be superimposed on the display image) is prestored in the nonvolatile memory 9 in association with the information about the inspection region.

In step S802, the CPU 7 estimates the position and orientation of the subject body (human body) through the image analysis processing based on the image from the camera 3 acquired as an outer appearance image. According to the present exemplary embodiment, the CPU 7 outputs skeletal information including the position coordinates of a feature point of each joint as the position and orientation information for the subject body (human body). Examples of joints include the nose, neck, right shoulder, right elbow, right wrist, left shoulder, left elbow, left wrist, central buttock, right buttock, right knee, right ankle, left buttock, left knee, left ankle, right eye, left eye, right ear, left ear, left thumb, left little finger, left heel, right thumb, right little finger, and right heel. The CPU 7 uses a learner trained through a machine learning (deep learning) method as means for obtaining the skeletal information based on an image. According to the present exemplary embodiment, the CPU 7 uses a learning model (learner) trained with a set of a plurality of training images including a human body as a subject and correct answer information for skeletal information (probability distribution of joints) with respect to each training image. This method makes it possible to obtain the skeletal information in two-dimensional (2D) or three-dimensional (3D) coordinates regardless of whether information obtained from the camera 3 (including a stereo camera, infrared camera, and TI/F camera) is only a luminance image, only a depth image, or both images. Examples of known learners of this type include Openpose (registered trademark) of Carnegie Mellon University. According to the present exemplary embodiment, position and orientation information (skeletal information) estimated by the learner trained through machine learning is stored in a memory in array or list form. More specifically, for a plurality of regions such as the above-described joints, information indicating the distribution of the probability that each region exists in an image is output as estimated position and orientation information. When the distribution (probability distribution) of the reliability that a region n (n is an integer) exists in an image is Rn(x, y), the output R as skeletal information is represented by R={Rn(x, y)|n=1, 2, . . . , N (N is an integer)}. Rn(x, y) does not need to be the reliability distribution for the entire area on the image but may be the reliability distribution only for an area having a reliability larger than a threshold value. Alternatively, Rn(x, y) may be stored only a peak value of the reliability in association with the coordinates (e.g., region 3: right shoulder, reliability: 0.5, coordinates: (x, y)=(122, 76)).

Figure 15B:
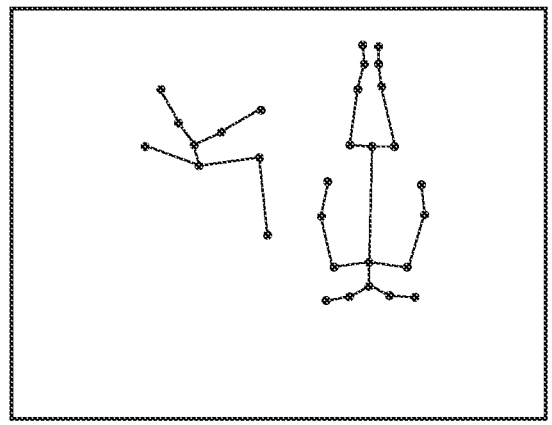

The CPU 7 extracts the position of the peak value of the reliability for each region (i.e., position at which each region is detected with the highest probability of existence) by using the output R. FIG. 15B illustrates an example of skeletal information visualized based on this information.

As preprocessing of obtaining the skeletal information by using the learner trained with images, the present exemplary embodiment performs image quality correction such as noise rejection, distortion correction, color conversion, and luminance and color gradation correction, and performs image rotation and flipping. Parameters for image correction are tabulated based on, for example, the model of the camera 3 and an imaging condition, and then prestored in the nonvolatile memory 9. The correction processing is performed on input outer appearance image by using these correction parameters to bring the imaging condition close to the imaging condition of images of the data set used in training, so that the estimation is performed with higher accuracy. For example, when an image captured in a dark room is corrected to a brighter image, high-sensitivity noise may occur, resulting in a different tendency from the data set used in learning. In such a case, it is desirable that processing of removing high-sensitivity noise be performed on the input outer appearance image. Likewise, in a case where the lens of the camera 3 is a wide-angle lens having a large peripheral distortion, it is desirable that the distortion correction be performed on the input outer appearance image. In addition, in a case where all images in the data set includes the head at the top, it is desirable that an image be rotated or flipped so that the head comes to the top and the resultant be input. If the training is performed by using images converted through certain processing, it is desirable that the input image be converted before input to the learner.

As illustrated in FIG. 15B, skeletal information for the inspector and neighboring persons may also be acquired together in step S802. Thus, in step S803, the CPU 7 identifies the skeletal information for the subject based on the image of the skeletal information acquired in step S802.

Conceivable methods for identifying the skeletal information about the subject include the following examples. One method is to combine with face recognition processing. The CPU 7 authenticates the inspector's face pre-registered in the nonvolatile memory 9 from the outer appearance image. The skeletal information about the inspector and the skeletal information about the subject are then identified from the distance relation between the position where the inspector's face is authenticated and detected and the portions detected as facial regions (such as eyes, nose, and ears) in the skeletal information detected in step S802.

As another method, the CPU 7 may identify the ultrasonic diagnostic apparatus body 1 and distinguish between the inspector and the subject based on the planar (X- and Y-directional) or three-dimensional (Z-directional) distance relation from the ultrasonic diagnostic apparatus body 1. As still another method, the CPU 7 identifies the orientation type based on the positional relation between joint points in the skeletal information to distinguish between the inspector and the subject. As still another method, a procedure is set so that the subject is image-captured in a predetermined area in adjusting the angle of field of the camera 3, and the CPU 7 identifies the subject based on the position in the skeletal information.

Figure 15C:
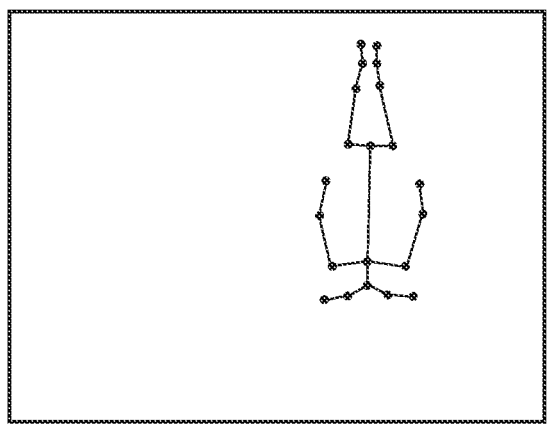

According to the present exemplary embodiment, the CPU 7 performs processing through at least one of the above-described identification methods to identify the inspector and the subject and visualize the position and orientation information for the identified subject, as illustrated in FIG. 15C.

Figure 15D:
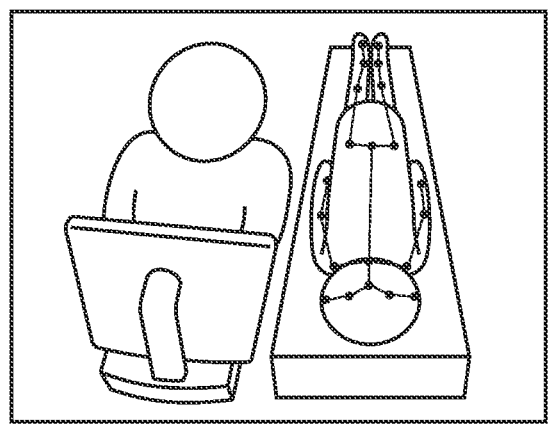
Figure 17:
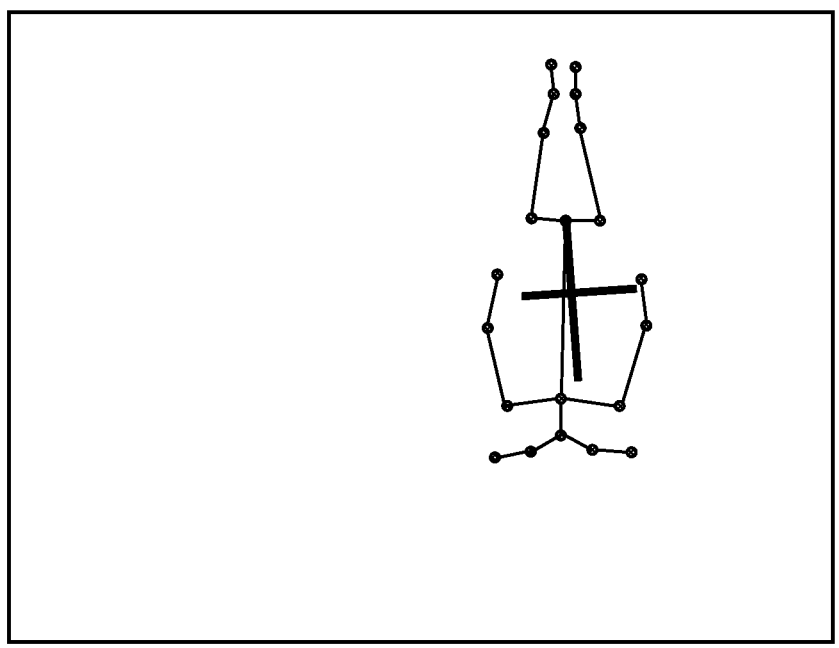
FIG. 17 illustrates an image in which skeletal information as a result of estimating the position and orientation of the human body and a cross line as a result of estimating the position and orientation of the probe are superimposed according to the first exemplary embodiment.

In step S804, the CPU 7 displays on the display 5 an image in which the position and orientation information for the subject thus estimated is superimposed on the display image from the camera 3, as illustrated FIG. 15D.

For the image to be displayed on the display 5, the CPU 7 may not directly use the image captured by the camera 3. Instead, in consideration of privacy, the CPU 7 may replace the image with an avatar or animation or convert the image into a 3D model through known image processing.

In step S805, the CPU 7 determines whether the freeze button 6a is pressed. If the freeze button 6a is pressed by the inspector (YES in step S805), the CPU 7 ends the update of the estimation result for the skeletal information (position and orientation information) for the subject based on the outer appearance images sequentially displayed on the display 5. The processing then proceeds to step S806. If the freeze button 6a is not pressed (NO in step S805), the processing returns to step S801. The CPU 7 continues the estimation of the position and orientation information.

After the freeze button 6a is pressed (YES in step S805), then in step S806, if the inspector makes sure that there is no problem in the estimation result for the position and orientation information displayed on the display 5 and then operates the finalization button 6b, the CPU 7 ends the processing for estimating the position and orientation of the subject body. If the desired result of the position and orientation is not acquired (NO in step S806), the processing returns to step S801. Then, the CPU 7 repeatedly performs processing for estimating the position and orientation.

In step S806, the CPU 7 waits for the confirmation by the inspector in order to address a case where the orientation of the subject is not the desired one, a case where the camera angle is not preferable, or a case where the result of detecting the position and orientation is remarkably different from the visually confirmed position and orientation.

In other exemplary embodiments, steps S805 and S806 may be omitted (ignored). More specifically, the position and orientation information for the subject body (human body) may be kept being updated at predetermined time intervals until the inspector determines that the processing for identifying the inspection region in the subsequent stage is suitable and then performs the finalizing operation.

Although, in the present exemplary embodiment, the CPU 7 uses the skeletal information (joint information) as a method for estimating the position and orientation of the subject body (human body), the CPU 7 may estimate the 3D shape of the subject body based on mesh-formed information. Such a technique can be implemented by using machine learning (a learner). More specifically, this method may use a learner that trained by using a set of a plurality of training images including the subject and correct answer information for the mesh-formed information for each training image.

Figure 9:
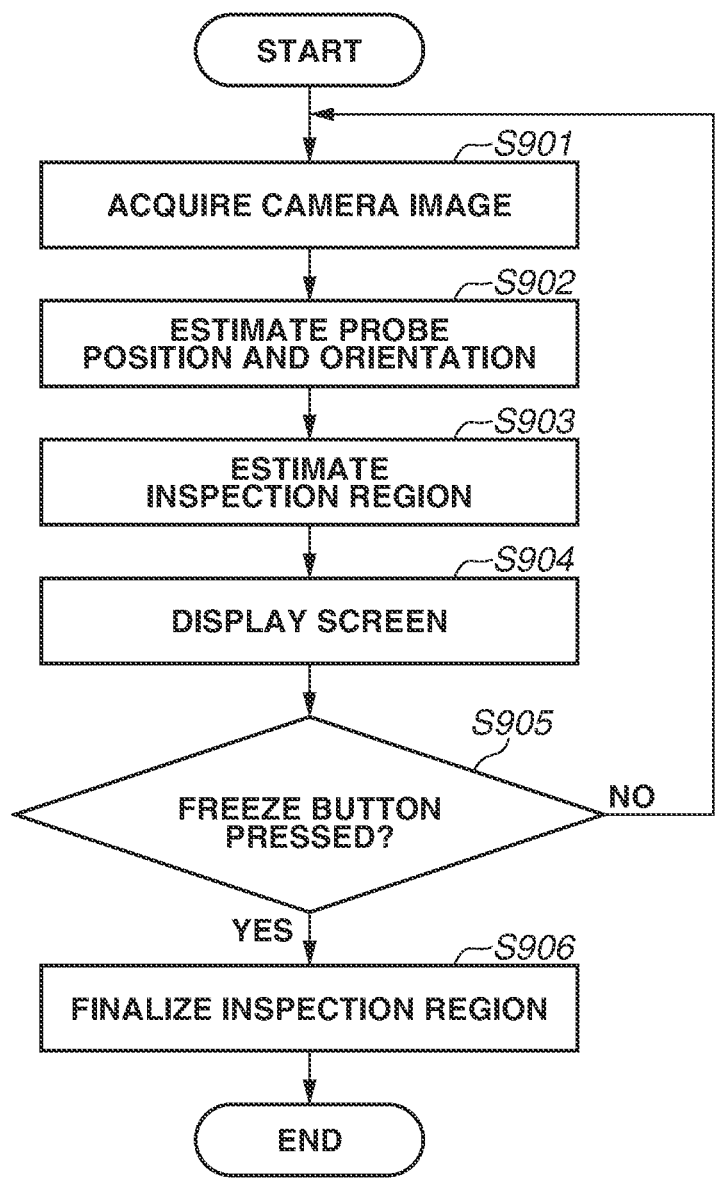
FIG. 9 is a flowchart illustrating processing for inspection region identification A according to the first exemplary embodiment.

FIG. 9 is a flowchart illustrating a detailed operation of the inspection region identification A in step S702 illustrated in FIG. 7. Each operation in the following steps is executed by the CPU 7 or each unit under the instruction of the CPU 7.

In step S901, the CPU 7 acquires an outer appearance image (image data) including the ultrasonic probe 2 from the camera 3 via the communication I/F of the camera control unit 15. An image may be captured without change since the angle of view of the camera 3 has been adjusted to include the subject in the previous step. However, at least one of pan control, tilt control, and zoom control may be performed to achieve an angle of view at which the ultrasonic probe 2 is easier to be detected. FIG. 16 illustrates a change in the angle of view of the camera 3 in a case where the angle of view is adjusted from the outer appearance image centering on the subject to the angle of view centering on the ultrasonic probe 2, and a captured image.

In step S902, the CPU 7 analyzes the acquired outer appearance image to obtain the position and orientation of the ultrasonic probe 2. More specifically, the CPU 7 detects a plurality of Argument Reality (AR) markers (a plurality of corners is provided on each marker) provided on the ultrasonic probe 2 through image recognition processing including filter processing, binary processing, determination processing, and shape recognition processing for edge detection based on the outer appearance image. The CPU 7 may subject the outer appearance image acquired by the camera 3 to sharpness adjustment, gain adjustment, noise reduction, and other image processing to perform image recognition with higher accuracy. The CPU 7 detects the AR markers provided on the ultrasonic probe 2 and calculates the position and orientation of the ultrasonic probe 2 based on the positional relation of a plurality of corners existing on the detected AR markers, sizes of drawings formed by the corners, and distortion conditions. Since the ultrasonic probe 2 is rigid, the relation between each AR marker and the inspection surface of the ultrasonic probe 2 can be obtained through calculation. As illustrated in FIGS. 16 and 19B, it is desirable that a plurality of AR markers (desirably at least three AR markers) is disposed on the marker attachment 203. The AR markers are disposed at predetermined intervals on the outer periphery of the ultrasonic probe 2 so that at least one of the AR markers captured by the camera 3 can be acquired regardless of the orientation of the ultrasonic probe 2 and the position of the connector 202. According to the present exemplary embodiment, the CPU 7 outputs the following data as an output regarding the position and orientation of the ultrasonic probe 2. The CPU 7 outputs position and orientation information including positional information (image coordinate information (x, y)) in the outer appearance image, positional information (x, y, z) in the three-dimensional real space with reference to the camera 3, and vector information (direction vector d=(x, y, z)) representing the orientation of the probe 2. The positional information (x, y) is used for processing for identifying the inspection region in step S903. The position and orientation information (x, y, z), d is used for performing display such that the position and orientation of the probe 2 with respect to the inspection region in the body mark in the screen displayed on the display 5 in step S904 is visually identified. However, the use of the position and orientation information is not limited thereto. The CPU 7 may use the position and orientation information in the processing for identifying the inspection region and may display only the positional information in the display processing.

If the position and orientation of the ultrasonic probe 2 can be obtained through calculation, the CPU 7 may use light emitting diodes (LEDs), retroreflection marks, and any other marks, instead of AR markers, as criteria (indexes) for obtaining the position and orientation of the ultrasonic probe 2.

Since the ultrasonic probe body 201 generally has a rigid body and thus the position and orientation thereof are limited, the ultrasonic probe body 201 detects the position and orientation through rule-based processing, i.e., image recognition using predetermined patterns such as AR markers. This makes it possible to easily achieve high detection accuracy and obtain the position and orientation with lower processing cost and higher processing speed than those of the technique using a learner trained through machine learning.

In step S903, the CPU 7 identifies the inspection region based on the relation between the estimation result (R) for the position and orientation of the subject obtained in step S701 and stored in the memory 8 and the positional information (x, y) for the ultrasonic probe 2 obtained in step S902. According to the present exemplary embodiment, the CPU 7 outputs a plurality of inspection region candidates as a result of identification, starting from the inspection region having the highest evaluation value for the inspection region in each piece of skeletal information.

The following methods are applicable for a method for identifying the inspection region in a case where skeletal information R has been acquired as position and orientation information for the subject.

For example, the CPU 7 extracts the position having a peak value of the reliability in the reliability distribution Rn(x, y) for each region, i.e., the coordinates of the position having the highest reliability for each region (simply referred to as the coordinates of each region). The CPU 7 then identifies the inspection region based on the coordinates of each region and the distance from the positional information (Euclid/Mahalanobis distance) about the ultrasonic probe 2. More specifically, the CPU 7 calculates the evaluation value so that the evaluation value increases with decreasing distance between the coordinates of each region and the ultrasonic probe 2. The CPU 7 also calculates the evaluation value for each region so that a greater weight is applied as a reliability corresponding to the coordinates of each region increases. The CPU 7 then sequentially extracts inspection region candidates from among a plurality of regions, starting from the region having the relatively highest evaluation value. In the evaluation value calculation, the CPU 7 may refer to only either one of the distance from the position of the ultrasonic probe 2 and the reliability distribution for each region.

The CPU 7 may calculate the evaluation value in each area in the image by using the reliability distribution Rn(x, y) for each region. More specifically, the CPU 7 may calculate the evaluation value distribution determined with Rn(x, y)*(Weight based on the distance from the ultrasonic probe 2) for each region, and then identify the position having the highest evaluation value and the region at that position as an inspection region.

Examples of other methods for identifying the inspection region include calculating the evaluation value based on the distance between a straight line connecting the positions of the above-described regions and the positional information (x, y) about the ultrasonic probe 2, and the reliability distribution of the two regions corresponding to the straight line.

Examples of still other methods for identifying the inspection region include calculating the evaluation value based on the coordinates obtained by dividing the positions of a plurality of regions by a certain ratio, the distance from the positional information (x, y) for the ultrasonic probe 2, and the reliability distribution of the regions at two points of the division source.

Examples of still other methods for identifying the inspection region also include generating a closed 2D or 3D domain by using the points obtained with a certain ratio based on the relation between a plurality of joints, and then calculating the evaluation value by subjecting the closed domain to inside/outside determination on the positional information (x, y) about the ultrasonic probe 2.

The CPU 7 may calculate the evaluation value by combining a part or all of the plurality of the above-described methods.

In step 903, the position and orientation of the subject stored in the memory 8 may be different from the current position and orientation of the subject because the subject has moved after execution of step 701. Inspection regions identified by using different position and orientation may be an incorrect result. Thus, the CPU 7 may determine whether the subject is moving, and, if a movement is detected, the processing returns to step 701. The CPU 7 may estimate the position and orientation of the subject body again.

Examples of methods for determining whether the subject is moving include using a differential image or using an optical flow.

In a case where a differential image is used, for example, the CPU 7 subjects a portion of the inspector's hand and the probe 2 to mask processing. Then, in the images acquired in steps S801 and S901, the CPU 7 determines whether the remaining portion has changed in the luminance value and hue by an amount equal to or larger than threshold values. In such a case, the CPU 7 may detect the above-described changes through statistical processing.

In a case where an optical flow is used, for example, the CPU 7 registers as a pattern the subject body (human body) in the camera image that is acquired in step S801 when the position and orientation of the subject body is estimated. The CPU 7 then subjects the camera image in step S901 to template matching to detect the movement. Alternatively, the CPU 7 temporarily stores the camera image acquired in step S801 in the memory 8. Then, the CPU 7 calculates the amount of movement of a feature point determined through SHIFT and AKAZE in the image acquired in step S901 and between the two images, thus detecting the movement of the human body in an image. In addition, known tracking methods such as KCF tracker is also applicable.

In step S904, the CPU 7 displays the inspection region identified in step S903 on the display 5. In step S905, the CPU 7 determines whether the inspector performs an operation corresponding to OK on the control panel 6 or presses the freeze button 6a on the ultrasonic probe 2.

Figure 21:
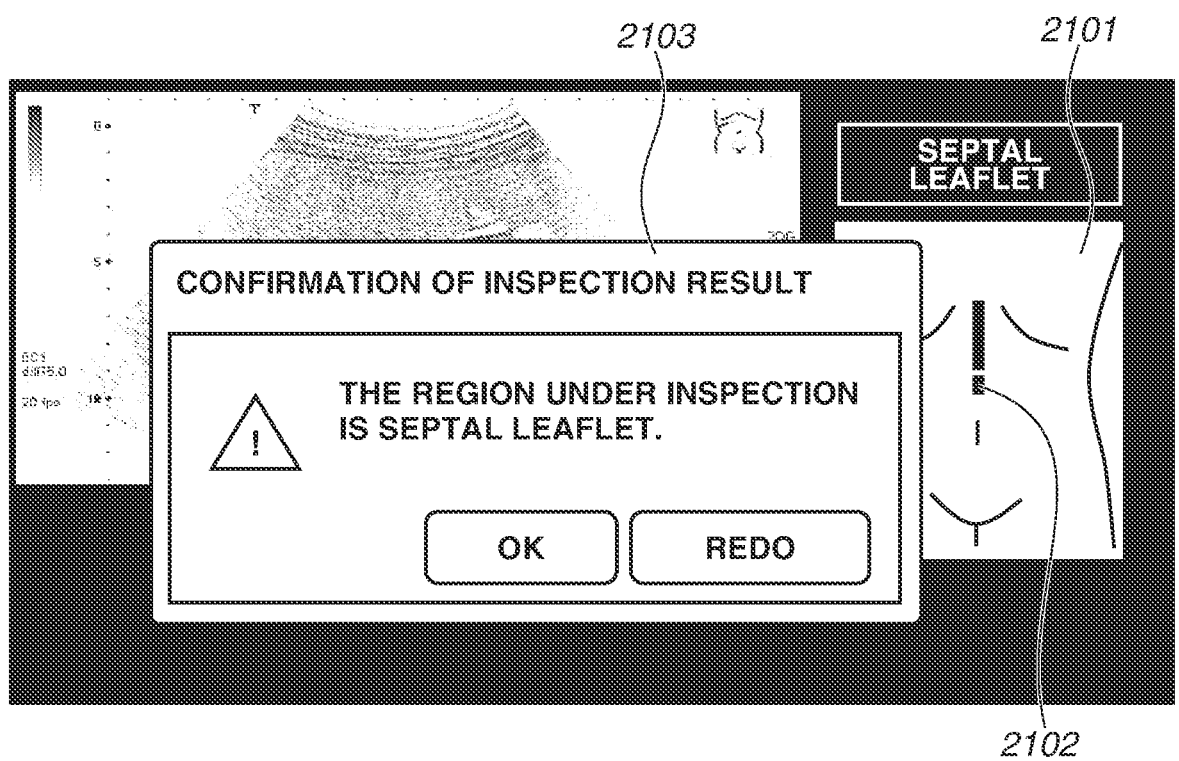
FIG. 21 illustrates an image of a display output result obtained in measurement using an inspection system according to the third modification of the first exemplary embodiment.

FIG. 21 illustrates an example of a screen displayed on the display 5 when the inspector acknowledges the result of the inspection region identification in step S905. The CPU 7 displays the superposition of a body mark 1901 of the GUI corresponding to the subject body and a probe mark 2102 of the GUI corresponding to the ultrasonic probe 2 at the position of the corresponding inspection region. In such a case, both the body mark and the probe mark may be displayed if the name of the inspection region has been identified ("Septal Leaflet" in FIG. 21). The screen displays an inspection result confirmation window including an OK and a Redo icon button. The inspector selects the OK or the Redo button by using the control panel 6 or presses the freeze button 6a on the ultrasonic probe 2 to finalize the inspection region or issue a redo instruction. If the inspector selects the OK button or presses the freeze button 6a (YES in step S905), the CPU 7 ends the series of processing. If the inspector selects the Redo button or does not presses the freeze button 6a (NO in step S905), the processing returns to step S901. The CPU 7 repeats the processing for identifying the inspection region.

While the window for promoting the inspection result confirmation illustrated in FIG. 21 in step S905 is being displayed, the processing for estimating the inspection region may be suspended. The finalization processing in step S905 may be omitted, and the processing of finalizing the inspection region may be performed at an optional timing in steps S701 to S704.

In step S906, the CPU 7 finalizes the inspection region identified in step S903 in response to an inspector's operation. The inspector confirms the inspection region displayed on the display 5 and, if the desired inspection region is obtained, operates a predetermined operating member of the control panel 6 or presses the finalization button 6b on the ultrasonic probe 2. If the identified inspection region is wrong, the inspector operates the control panel 6 to display the second and third region candidates on the display 5. Then, when the inspector selects an inspection region candidate, the selected inspection region candidate is finalized.

Figure 10:
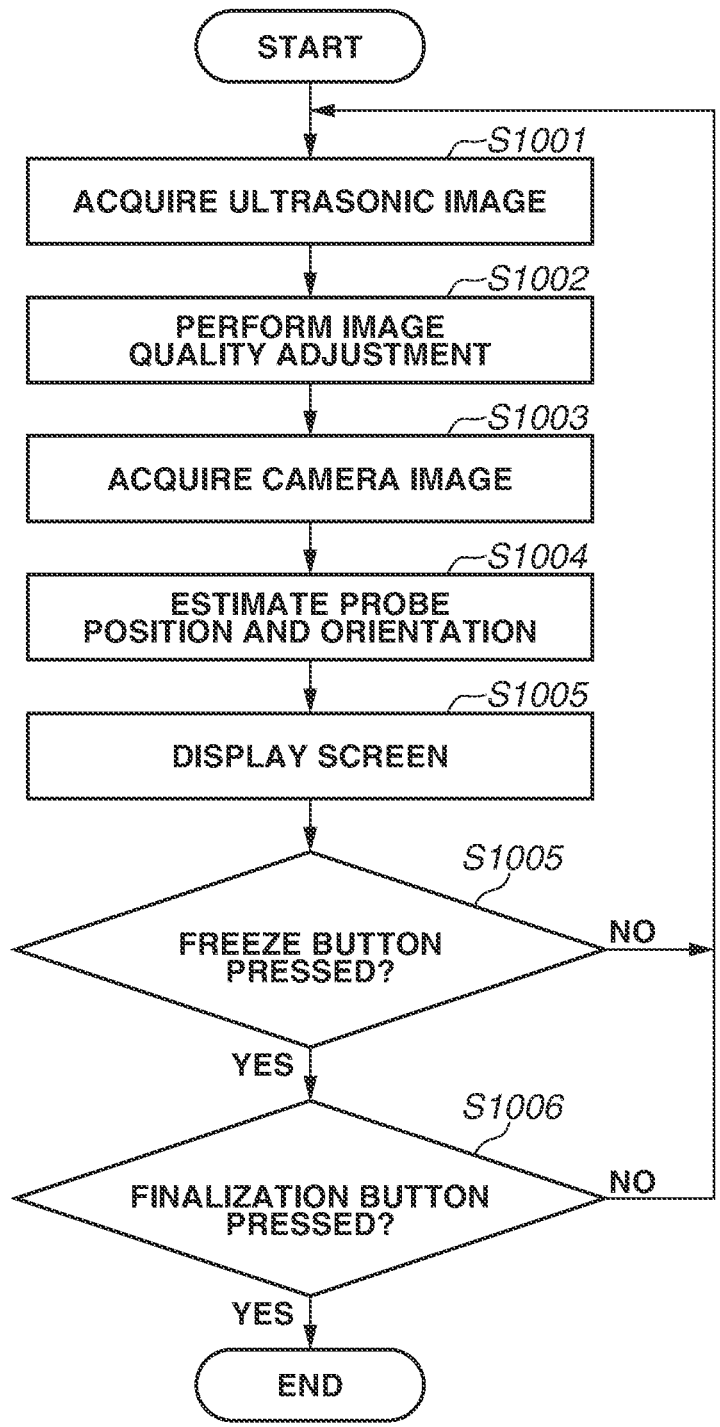
FIG. 10 is a flowchart illustrating post-measurement processing according to the first exemplary embodiment.

FIG. 10 is a flowchart illustrating in detail a flow of the ultrasonic image capturing in step S703 illustrated in FIG. 7.

FIG. 10 illustrates processing that combines the ultrasonic image processing illustrated in FIG. 6 and the processing of inspection region identification A illustrated in FIG. 9. For steps performing basically the same operations as the processing of the flowcharts illustrated in FIGS. 6 and 9, the descriptions will be omitted. Step S1001 corresponds to step S601, step S1002 corresponds to step S602, step S1003 corresponds to step S901, step S1004 corresponds to step S902, step S1005 corresponds to step S904, step S1006 corresponds to step S603, and step 1007 corresponds to step S604.

Figure 11:
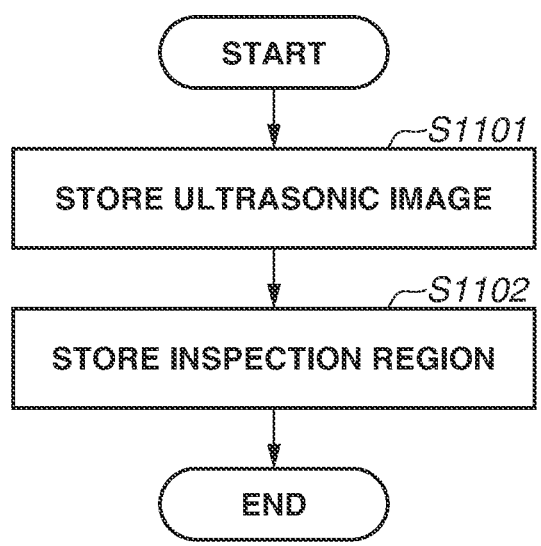
FIG. 11 is a flowchart illustrating the measurement processing according to a second modification of the first exemplary embodiment.

FIG. 11 is a flowchart illustrating in detail a flow of the post-measurement processing in step S704 illustrated in FIG. 7. Each of the following steps is executed by the CPU 7 or each unit under the instruction of the CPU 7.

In step S1101, the CPU 7 stores the ultrasonic image finalized in step S1007 in the nonvolatile memory 9 or an external medium, or transmits data to the outside.

In step S1102, the CPU 7 stores the information about the inspection region finalized in step S906 and the position and orientation information (collectively referred to as inspection region information) about the probe 2 in the nonvolatile memory 9 or an external medium, or transmits data to the outside in association with the ultrasonic image in step S1101. Examples of information about the inspection region and information about the position and orientation of the probe 2 include the name of the inspection region, the body mark, and the position and orientation information for the probe mark with respect to the body mark. The position and orientation information for the probe mark may be stopped at the angle on the two-dimensional image or may be three-dimensional orientation information. The inspection region information does not necessarily need to include the position and orientation information for the probe 2.

(Second Modification)

Figure 12:
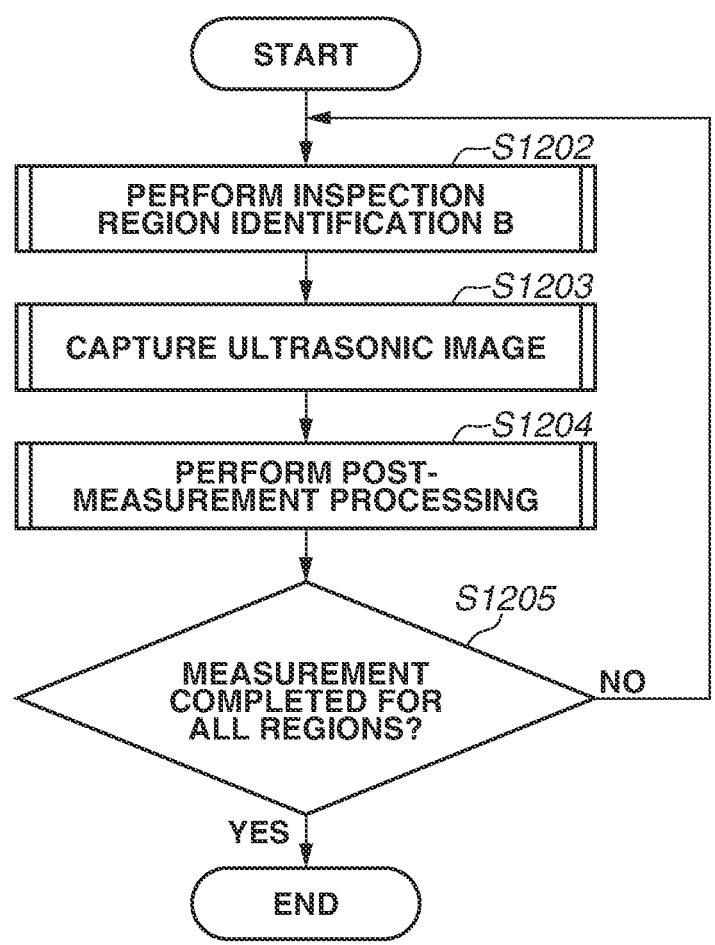
FIG. 12 is a flowchart illustrating processing for inspection region identification B according to the first exemplary embodiment.

FIG. 12 is a flowchart illustrating another form of step S404 illustrated in FIG. 4 in a case where the inspector makes the setting for automatically setting the inspection region. Step S1203 corresponds to step S703, step S1204 corresponds to step S704, and step S1205 corresponds to step S705. For steps performing basically the same operations as the processing of the flowchart illustrated in FIG. 7, descriptions thereof will be omitted.

In this flowchart, as in the flowchart illustrated in FIG. 7, the CPU 7 automatically sets the inspection region performed based on an inspector's operation in step S503 illustrated in FIG. 5.

Figure 13:
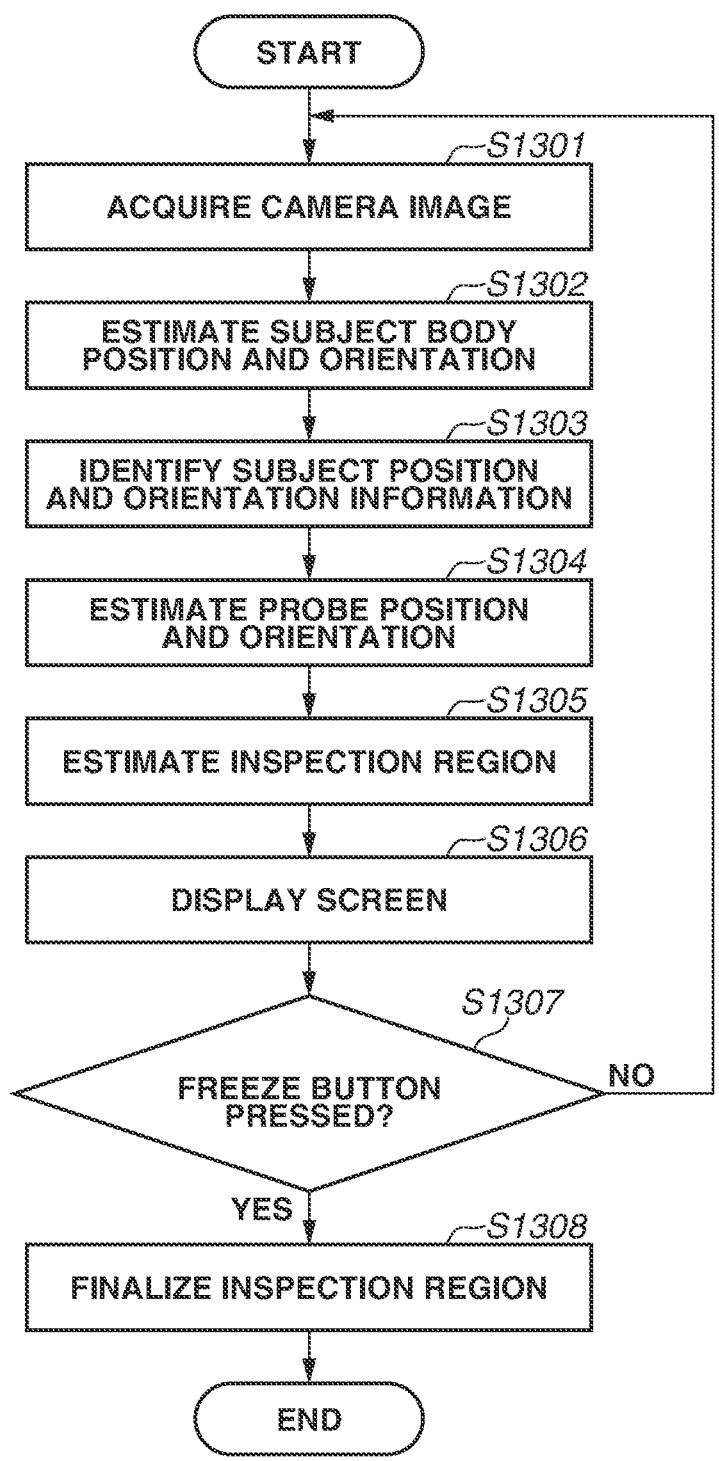
FIG. 13 is another flowchart illustrating processing for inspection region identification B according to the first exemplary embodiment.
Figure 14:
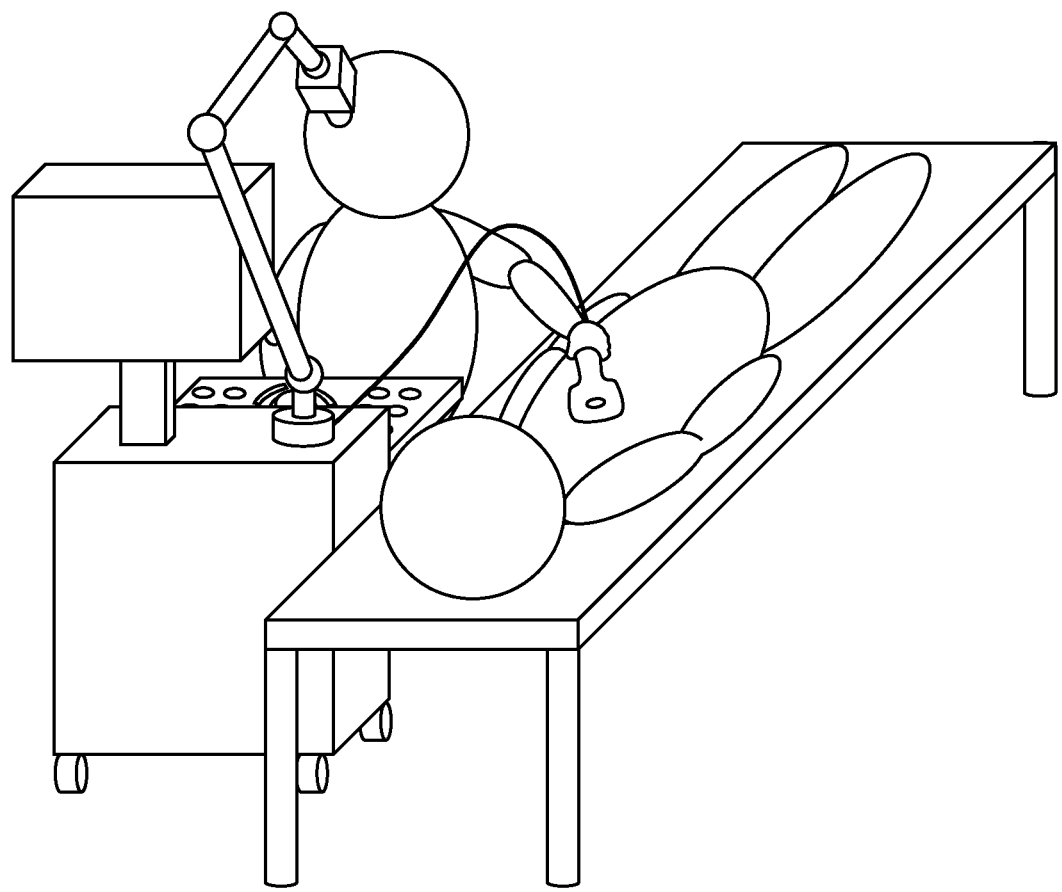
FIG. 14 illustrates an image of measurement using the inspection system according to the first exemplary embodiment.

FIG. 13 is a flowchart illustrating a detailed flow of inspection region identification B in step S1202 illustrated in FIG. 12. For steps performing basically the same operations as the processing of the flowcharts illustrated in FIGS. 8 and 9, descriptions will be omitted.

FIG. 13 illustrates processing that combines the processing for estimating the position and orientation of the subject body illustrated in FIG. 8 and the inspection region identification A illustrated in FIG. 9. Step S1301 corresponds to step S901, step S1302 corresponds to step S802, step S1303 corresponds to step S803, step S1304 corresponds to step S902, step S1305 corresponds to step S903, step S1306 corresponds to step S904, step S1307 corresponds to step S905, and step S1308 corresponds to step S906. The flowchart illustrated in FIG. 13 differs from the flowchart illustrated in FIG. 9 in that steps S802 and S803 illustrated in FIG. 8, which correspond to processing for estimating the position and orientation of the subject body, are added. Referring to the flowchart illustrated in FIG. 7, this processing is performed outside the flowchart.

In the processing illustrated in FIG. 13, the CPU 7 performs processing for estimating the position and orientation of the subject body and estimating the position and orientation of the probe 2 from a single outer appearance image acquired in a single image capturing, unlike the processing illustrated in FIG. 7, to estimate the inspection region. This enables reducing the number of inspector's operations for pressing the freeze button 6a and pressing the finalization button 6b. However, there arises an issue that, in a case where subject's inspection regions and the ultrasonic probe 2 cannot be image-captured at the same time, the inspection region identification becomes difficult. For example, the inspection region may be hidden by the ultrasonic probe 2 or the inspector. By contrast, in the processing illustrated in FIG. 7, the camera image for estimating the position and orientation of the subject body is different from the camera image for estimating the position and orientation of the probe 2, making it comparatively easier to avoid the issue.

(Third Modification)

A modification of the processing for identifying the inspection region performed in step S703 illustrated in FIG. 7, step S1102 illustrated in FIG. 11, and steps S1302 and S1304 illustrated in FIG. 13 will be described below. According to the above-described exemplary embodiment, the CPU 7 performs each operation assuming the inspection region identification for the entire human body. However, this also applies to a local inspection target, such as a hand.

For example, ultrasonographic inspection targeting a symptom of rheumatism is performed on joints of hands and feet of the subject. Thus, the learner trained for estimation of the position and orientation of a human body according to the present modification targets a localized inspection region. Generally, a learner for outputting information about the skeletal frame (joints) of hands and feet from an input image is used, which is different from a learner targeting the entire human body. Alternatively, a learner capable of detecting the skeletal frame of the human body, hands, and feet at the same time may be used.

As described above, since a plurality of candidates of localized inspection targets, e.g., hands and feet, is presumed, there is prepared a plurality of learners each corresponding to respective regions to detect the skeletal information for each region. In performing processing for identifying the inspection region, it is desirable that switching of the plurality of prepared learners is automatically performed based on and the outer appearance image acquired by the camera 3, or that information about the target region be selected and input in advance through an inspector's operation and switching of the plurality of prepared learners is performed.

A hand has five fingers (thumb, index finger, middle finger, fourth finger, and little finger) each of which has the first to the fourth joints. The trained learner according to the present modification estimates the position for each joint.

The output of the skeletal information may include fingertips in addition to joints. The fourth joint is set as the same single point in a representative basis for all of the five fingers.

Figure 18:
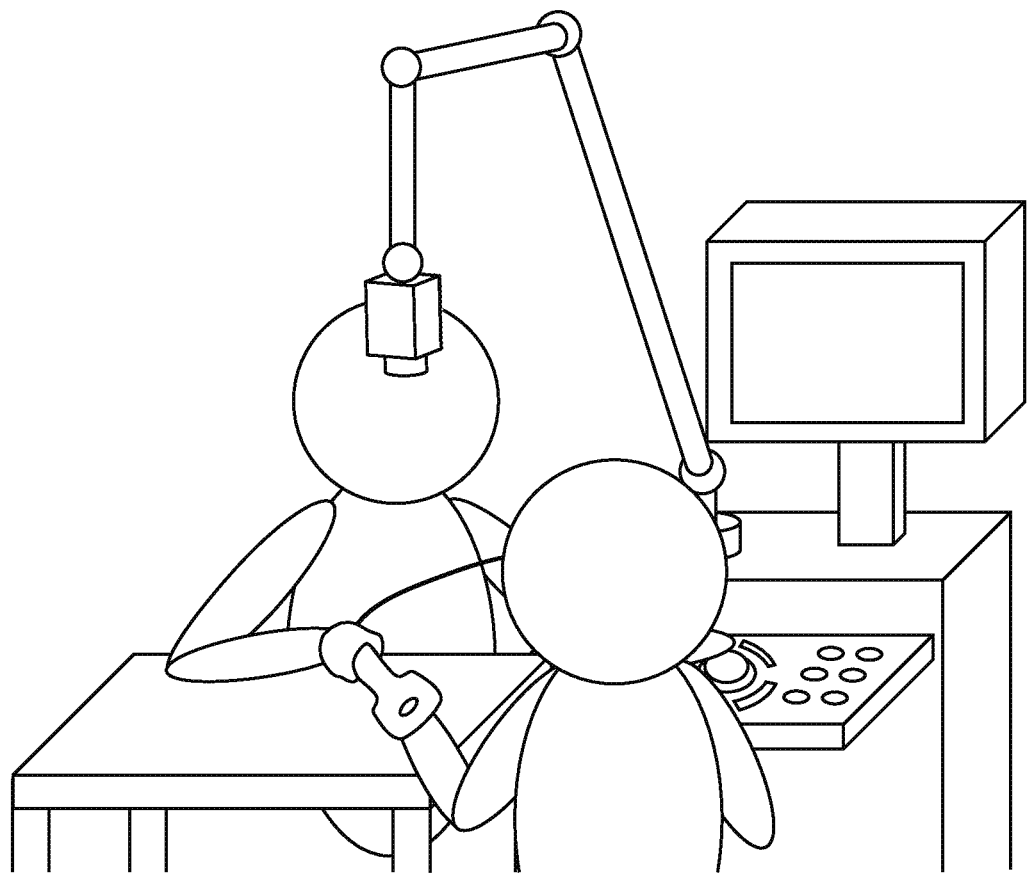
FIG. 18 illustrates an image of a screen displayed on a display in ultrasonic image measurement according to the first exemplary embodiment.
Figure 20:
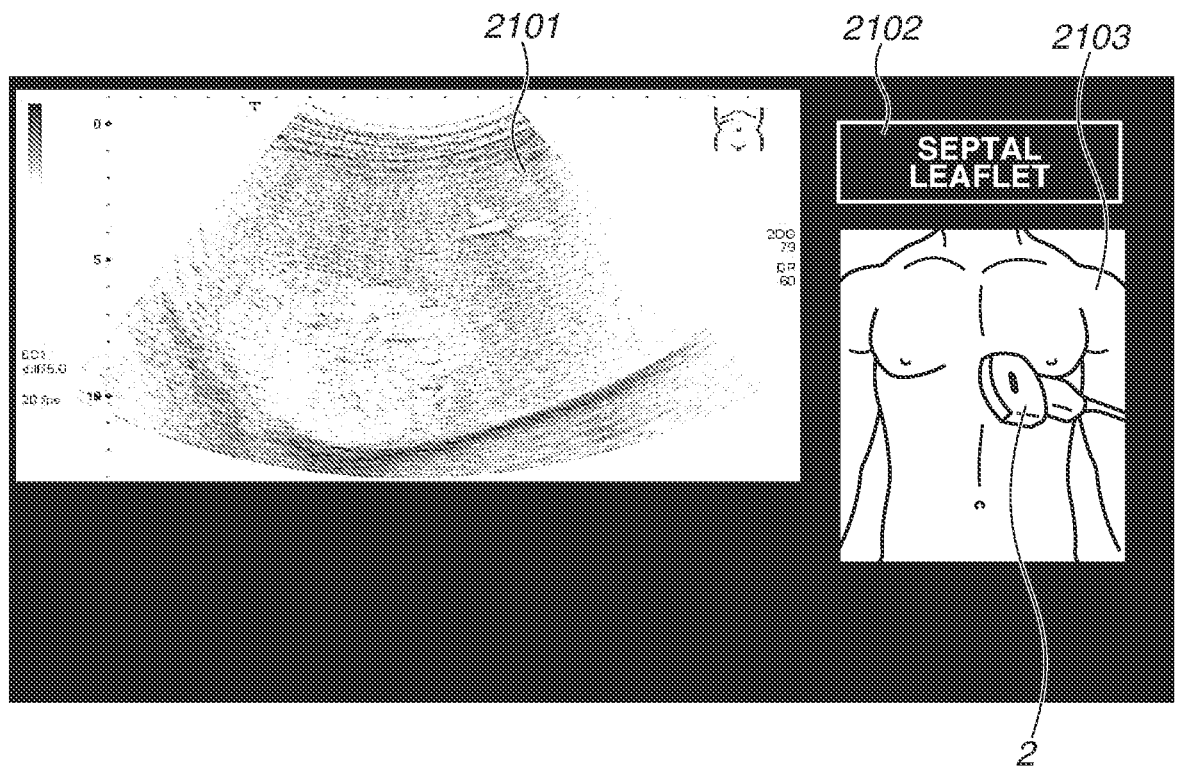
FIG. 20 illustrates an image of an inspection state according to a third modification of the first exemplary embodiment.

FIG. 18 illustrates an image of an inspection state when the inspection target region is any one region of the hand. The camera 3 is disposed and the position and orientation of the camera 3 are controlled so that the subject's inspection region and the ultrasonic probe 2 fit into the angle of view.

FIG. 19A illustrates an example of an image displayed on the display 5 in a hand inspection according to the present modification. The image is obtained by the CPU 7 estimating the skeletal information about a hand as the processing for estimating the position and orientation of the subject body, and superimposing the skeletal information on the outer appearance image obtained from the camera 3.

FIG. 19B illustrates an example of an image displayed on the display 5 in the hand inspection state according to the present modification. The image is obtained by the CPU 7 superimposing a result (cross line) of estimating the position and orientation of the probe 2 on the image acquired by the camera 3.

FIG. 19C illustrates an example of an image in which a result of estimating the position and orientation of the subject body and a result of estimating the position and orientation of the probe 2 are displayed together on the display 5. Through processing similar to the processing in step S903, it is possible to identify the inspection region, i.e., which joint of which finger.

As described above, according to the present exemplary embodiment, the CPU 7 estimates the detection of the position and orientation of a subject body (human body) in inspection by using a learner obtained through machine learning, and identifies the inspection region based on a result of this estimation and a result of estimating the position of an inspection device, thus achieving inspection region identification with higher accuracy.

According to the present exemplary embodiment, the CPU 7 performs detection processing with a lower processing load than that for the processing of detecting the position and orientation of a human body on a rule basis in estimating the position of the inspection device. This makes it possible to offer an inspection system having a low processing load while the system tracks the position of the probe 2 having a large amount and high frequency of movement.

The present exemplary embodiment also makes it possible to more smoothly identify the inspection region. The present exemplary embodiment also enables the inspector to perform operations while constantly grasping the region currently being inspected, preventing a region input failure.

(Other Exemplary Embodiments)

The object of the present disclosure can also be achieved by the following configuration. A storage medium storing a program code of software describing procedures for implementing the functions of the above-described exemplary embodiments is supplied to a system or apparatus. Then, a computer (or CPU or MPU) of the system or apparatus reads the program code stored in the storage medium and then executes the program code.

In such a case, the program code itself read from a storage medium implements new functions of the present disclosure, and the storage medium storing the program code and the program are also included in the present disclosure.

Examples of storage media for supplying a program code include a flexible disk, hard disk, optical disk, and magneto-optical (MO) disk. In addition, a compact disc read only memory (CD-ROM), compact disc recordable (CD-R), compact disk rewritable (CD-RW), digital versatile disc read only memory (DVD-ROM), digital versatile disc random access memory (DVD-RAM), digital versatile disc rewritable (DVD-RW), digital versatile disc recordable (DVD-R), magnetic tape, nonvolatile memory card, and ROM are also applicable.

The functions of the above-described exemplary embodiments are implemented by the computer making the read program code executable. Further, a case where an OS operating on the computer performs a part or all of actual processing based on instructions of the program code, and the functions of the above-described exemplary embodiments are implemented by the processing is also included in the present disclosure.

The following case is also included in the present disclosure. First of all, a program read from a storage medium is written in a memory included in a function expansion board inserted into the computer or a function expansion unit connected to the computer. Subsequently, a CPU included in the function expansion board or function expansion unit executes a part or all of actual processing based on instructions of the program code.

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2019-154070, filed Aug. 26, 2019, which is hereby incorporated by reference herein in its entirety.

What is claimed is:

1. An information processing apparatus comprising:
at least one processor; and
a memory storing instructions that, when executed by the at least one processor, cause the at least one processor to:
acquire a first image including at least a part of an inspection device and a second image including at least a part of a subject, the first and the second images being captured by an imaging apparatus;
estimate, as a first estimation, a position of the inspection device based on the first image;
estimate, as a second estimation, position and orientation information for the subject based on the second image;
identify an inspection region of the subject from a result of the first estimation and a result of the second estimation; and
receive a first finalization instruction to finalize an inspection result to be recorded or output to an external apparatus based on sequentially acquired inspection results of the subject, and a second finalization instruction to finalize inspection region information to be recorded or output to the external apparatus in association with the inspection result,
wherein the second finalization instruction for the inspection region information is received before the first finalization instruction for the inspection result.

2. The information processing apparatus according to claim 1, wherein, before receiving the first finalization instruction for the inspection result, the sequentially acquired inspection results and the inspection region information based on the received second finalization instruction are displayed on a display device.

3. The information processing apparatus according to claim 1, wherein an output of the second estimation is the position and orientation information for the subject with the second image as an input, based on a learning model trained by using a plurality of training images including subjects similar to the subject.

4. The information processing apparatus according to claim 1, wherein an output of the first estimation is an estimate of the position of the inspection device through filter processing and shape recognition processing.

5. The information processing apparatus according to claim 1, wherein an output of the second estimation is skeletal information indicating a plurality of joint points of the subject and positions thereof as the position and orientation information for the subject.

6. The information processing apparatus according to claim 5, wherein execution of the instructions further configures the at least one processor to identify the inspection region of the subject based on a distance from the position of the inspection device estimated by the first estimation unit to the plurality of joint points.

7. The information processing apparatus according to claim 6, wherein execution of the instructions further configures the at least one processor to calculate an evaluation value by applying a larger weight to a joint point less distant from the position of the inspection device estimated by the first estimation, and identifies the inspection region of the subject based on the evaluation value calculated for each of the plurality of joint points.

8. The information processing apparatus according to claim 6,
wherein the second estimation outputs information about reliability for each of the plurality of joint points of the subject, and
wherein the inspection region of the subject is identified based on the information about the reliability.

9. The information processing apparatus according to claim 1, wherein a processing load associated with estimating the position of the inspection device using the first image during the first estimation is smaller than a processing load associated with estimating the position and orientation of the subject using the second image during the second estimation.

10. The information processing apparatus according to claim 1, wherein the first and the second images are acquired from an image acquired in a single image capturing.

11. The information processing apparatus according to claim 1, wherein the position of the inspection device is detected during the first estimation by detecting a marker disposed on the inspection device from the first image.

12. The information processing apparatus according to claim 1, wherein the position and orientation of the inspection device is detected during the first estimation by detecting a marker disposed on the inspection device from the first image.

13. The information processing apparatus according to claim 1, wherein the sequentially acquired inspection results are acquired via an ultrasonic probe.

14. An inspection system comprising:
an imaging apparatus configured to capture a first image including at least a part of an inspection device and a second image including at least a part of a subject;
at least one processor; and
a memory storing instructions that, when executed by the at least one processor, cause the at least one processor to:
inspect the subject;
estimate, as a first estimation, a position of the inspection device based on the first image;
estimate, as a second estimation, position and orientation information for the subject based on the second image;
identify an inspection region of the subject from a result of the first estimation and a result of the second estimation; and
receive a first finalization instruction to finalize an inspection result to be recorded or output to an external apparatus based on sequentially acquired inspection results, and a second finalization instruction to finalize inspection region information to be recorded or output to the external apparatus in association with the inspection result,
wherein the second finalization instruction for the inspection region information is received before the first finalization instruction for the inspection result.

15. An information processing method comprising:
acquiring a first image including at least a part of an inspection device and a second image including at least a part of a subject, the first and the second images being captured by an imaging unit;
estimating, as first estimating, a position of the inspection device based on the first image;
estimating, as second estimating, position and orientation information for the subject based on the second image;
identifying an inspection region of the subject from a result of the first estimating and a result of the second estimating; and
receiving a first finalization instruction to finalize an inspection result to be recorded or output to an external apparatus based on sequentially acquired inspection results of the subject, and a second finalization instruction to finalize inspection region information to be recorded or output to the external apparatus in association with the inspection result,
wherein, the second finalization instruction for the inspection region information is received before the first finalization instruction for the inspection result.

16. A non-transitory computer-readable storage medium storing instructions that, when executed by at least one processor of an information processing apparatus, configure the at least one processor of the information processing apparatus to perform operations comprising:
acquire a first image including at least a part of an inspection device and a second image including at least a part of a subject, the first and the second images being captured by an imaging apparatus;
estimate, as a first estimation, a position of the inspection device based on the first image;
estimate, as a second estimation, position and orientation information for the subject based on the second image;
identify an inspection region of the subject from a result of the first estimation and a result of the second estimation; and
receive a first finalization instruction to finalize an inspection result to be recorded or output to an external apparatus based on sequentially acquired inspection results of the subject, and a second finalization instruction to finalize inspection region information to be recorded or output to the external apparatus in association with the inspection result,
wherein the second finalization instruction for the inspection region information is received before the first finalization instruction for the inspection result.

* * * * *